(12) United States Patent
Moya

(10) Patent No.: US 8,163,886 B2
(45) Date of Patent: Apr. 24, 2012

(54) PURIFICATION OF PROTEINS

(75) Inventor: Wilson Moya, Concord, MA (US)

(73) Assignee: EMD Millipore Corporation, Billerica, MA (US)

( * ) Notice: Subject to any disclaimer, the term of this patent is extended or adjusted under 35 U.S.C. 154(b) by 256 days.

(21) Appl. No.: 12/004,314

(22) Filed: Dec. 20, 2007

(65) Prior Publication Data

US 2009/0036651 A1    Feb. 5, 2009

Related U.S. Application Data

(60) Provisional application No. 60/876,330, filed on Dec. 21, 2006.

(51) Int. Cl.
 A61K 39/395    (2006.01)
 C07K 16/00    (2006.01)
 C07K 1/32    (2006.01)
 C12P 21/08    (2006.01)

(52) U.S. Cl. ............... 530/390.1; 424/176.1; 424/177.1; 435/69.6; 435/70.1; 435/70.21; 436/548; 530/390.5; 530/421

(58) Field of Classification Search .................. None
See application file for complete search history.

(56) References Cited

U.S. PATENT DOCUMENTS

| | | |
|---|---|---|
| 4,371,674 A | 2/1983 | Hertel et al. |
| 4,515,893 A | 5/1985 | Kung et al. |
| 4,536,294 A | 8/1985 | Guillet et al. |
| 4,676,980 A | 6/1987 | Segal et al. |
| 4,780,409 A | 10/1988 | Monji et al. |
| 4,816,567 A | 3/1989 | Cabilly et al. |
| 4,828,701 A | 5/1989 | Cussler |
| 4,863,613 A | 9/1989 | Johnson et al. |
| 4,912,032 A | 3/1990 | Hoffman et al. |
| 5,003,047 A | 3/1991 | Yarmush |
| 5,091,313 A | 2/1992 | Chang |
| 5,164,057 A | 11/1992 | Mori et al. |
| 5,238,545 A | 8/1993 | Yoshioka et al. |
| 5,599,719 A | 2/1997 | Woiszwillo et al. |
| 5,622,700 A | 4/1997 | Jardieu et al. |
| 5,672,347 A | 9/1997 | Aggarwal et al. |
| 5,693,762 A | 12/1997 | Queen et al. |
| 5,714,338 A | 2/1998 | Wai Fei et al. |
| 5,721,108 A | 2/1998 | Robinson et al. |
| 5,725,856 A | 3/1998 | Hudziak et al. |
| 5,736,137 A | 4/1998 | Anderson et al. |
| 5,739,383 A | 4/1998 | Yoon et al. |
| 5,840,851 A | 11/1998 | Plomer et al. |
| 5,929,214 A | 7/1999 | Peters et al. |
| 5,994,560 A | 11/1999 | Yoon et al. |
| 5,998,588 A | 12/1999 | Hoffman |
| 6,024,955 A | 2/2000 | Asano et al. |
| 6,127,526 A | 10/2000 | Blank |
| 6,133,047 A | 10/2000 | Elaissari et al. |
| 6,258,275 B1 | 7/2001 | Freitag et al. |
| 6,372,141 B1 | 4/2002 | Okano et al. |
| 6,420,487 B1 | 7/2002 | Vaidya et al. |
| 6,454,950 B1 | 9/2002 | Tjerneld et al. |
| 6,521,341 B1 | 2/2003 | Elaissari et al. |
| 6,538,089 B1 | 3/2003 | Samra et al. |
| 6,565,872 B2 | 5/2003 | Wu et al. |
| 6,582,926 B1 | 6/2003 | Chilkoti |
| 6,641,735 B1 | 11/2003 | Yoshizako et al. |
| 6,689,836 B2 | 2/2004 | Vaidya et al. |
| 6,706,187 B1 | 3/2004 | Okano et al. |
| 6,737,235 B1 | 5/2004 | Cros et al. |
| 6,765,081 B2 | 7/2004 | Lin et al. |
| 6,770,758 B2 | 8/2004 | Pan et al. |
| 6,805,793 B2 | 10/2004 | Yoshizako et al. |
| 6,821,515 B1 | 11/2004 | Eleland et al. |
| 6,830,670 B1 | 12/2004 | Viovy et al. |
| 6,852,819 B2 | 2/2005 | Ohnishi et al. |
| 6,858,694 B2 | 2/2005 | Ohnishi et al. |
| 6,863,437 B2 | 3/2005 | Ohnishi et al. |
| 6,867,268 B2 | 3/2005 | Vaidya et al. |
| 6,926,832 B2 | 8/2005 | Collins et al. |
| 6,956,077 B1 | 10/2005 | Akiyama et al. |
| 6,974,660 B2 | 12/2005 | Manias et al. |

(Continued)

FOREIGN PATENT DOCUMENTS

EP    0162034 B1    5/1985

(Continued)

OTHER PUBLICATIONS

Gil et al, Prog. Polym. Sci. 29, 1173-1222 (2004).*
Flocculation in Biotechnology and Separation Systems, 1987, pp. 351-368; Richard F. Unz; "Aspects of Bioflocculation: An Overview".*
Flocculation in Biotechnology and Separation Systems,1987, pp. 383-398; Karl Esser et al.; "Genetic Control of Flocculation of Yeast With Respect To Application in Biotechnology".*
Flocculation in Biotechnology and Separation Systems,1987, pp. 429-439; Chan Wha Kim et al; "Removal of Cell and Cell Debris By Electrostatic Adsorption of Positively Charged Polymeric Particles".*

(Continued)

Primary Examiner — David A Saunders
(74) Attorney, Agent, or Firm — Nields, Lemack & Frame, LLC

(57) ABSTRACT

The present invention relates to a selectively soluble polymer capable of binding to one or more constituents in a mixture containing various biological materials and the methods of using such a polymer to purify a biomolecule from such a mixture. The polymer is soluble in the mixture under a certain set of process conditions such as pH or temperature and is rendered insoluble and precipitates out of solution upon a change in the process conditions. While in its solubilized state, the polymer is capable of binding to a selected entity within the stream such as impurities (DNA, RNA, host cell protein, endotoxins, etc) in a cell broth and remains capable of binding to that entity even after the polymer is precipitated out of solution. The precipitate can then be filtered out from the remainder of the stream and the desired biomolecule is recovered and further processed.

16 Claims, 6 Drawing Sheets

U.S. PATENT DOCUMENTS

| | | | |
|---|---|---|---|
| 7,001,953 B2 | 2/2006 | Chen et al. |
| 7,011,930 B2 | 3/2006 | Manias et al. |
| 7,012,136 B2 | 3/2006 | Yamanaka et al. |
| 7,052,917 B1 | 5/2006 | Ohnishi et al. |
| 7,070,696 B2 | 7/2006 | Weir et al. |
| 7,083,948 B1 | 8/2006 | Sassenfeld et al. |
| 7,157,603 B2 | 1/2007 | Hilbrig |
| 7,169,908 B2 | 1/2007 | Lester et al. |
| 7,195,925 B2 | 3/2007 | Ohnishi et al. |
| 7,355,020 B2 | 4/2008 | Yamanaka et al. |
| 7,393,698 B2 | 7/2008 | Furukawa et al. |
| 7,422,724 B1 | 9/2008 | Manginell et al. |
| 7,429,458 B2 | 9/2008 | Chilkoti |
| 7,442,515 B2 | 10/2008 | Ratner et al. |
| 7,541,167 B2 | 6/2009 | Dave et al. |
| 7,553,658 B2 | 6/2009 | Kepka et al. |
| 7,625,764 B2 | 12/2009 | Stayton et al. |
| 7,632,656 B2 | 12/2009 | Kanazawa et al. |
| 7,695,905 B2 | 4/2010 | Furukawa et al. |
| 2002/0058786 A1 | 5/2002 | Chivers et al. |
| 2002/0098567 A1 | 7/2002 | Vaidya et al. |
| 2003/0059840 A1 | 3/2003 | Chilokoti et al. |
| 2003/0186293 A1 | 10/2003 | Ohnishi et al. |
| 2004/0010163 A1 | 1/2004 | Hilbrig |
| 2004/0039177 A1 | 2/2004 | Yamanaka et al. |
| 2004/0134846 A1 | 7/2004 | Akiyama et al. |
| 2005/0158782 A1 | 7/2005 | Furukawa et al. |
| 2005/0175702 A1 | 8/2005 | Muller-Schulte |
| 2005/0224415 A1 | 10/2005 | Akiyama et al. |
| 2006/0121519 A1 | 6/2006 | Patchornik |
| 2006/0189795 A1 | 8/2006 | Van Alstine et al. |
| 2006/0251610 A1 | 11/2006 | Nakahama |
| 2007/0148437 A1 | 6/2007 | Muller-Schulte |
| 2007/0193954 A1 | 8/2007 | Busson |
| 2007/0224241 A1 | 9/2007 | Stayton et al. |
| 2008/0160559 A1 | 7/2008 | Carre et al. |
| 2008/0193981 A1 | 8/2008 | Fahrner et al. |
| 2008/0220531 A1 | 9/2008 | Stayton et al. |
| 2008/0255027 A1 | 10/2008 | Moya et al. |
| 2008/0293118 A1 | 11/2008 | Furukawa et al. |
| 2008/0293926 A1 | 11/2008 | Hallgren et al. |
| 2009/0001025 A1 | 1/2009 | Takahashi et al. |
| 2009/0036651 A1 | 2/2009 | Moya |
| 2009/0148961 A1 | 6/2009 | Luchini et al. |
| 2009/0232737 A1* | 9/2009 | Moya et al. .................... 424/9.1 |
| 2009/0233327 A1 | 9/2009 | Lau et al. |
| 2010/0193148 A1 | 8/2010 | Mckay et al. |
| 2010/0282425 A1 | 11/2010 | Karppi et al. |

FOREIGN PATENT DOCUMENTS

| | | |
|---|---|---|
| EP | 534016 A1 | 3/1993 |
| EP | 0420937 | 11/1994 |
| EP | 0922715 | 11/2003 |
| WO | WO 92/20373 | 11/1992 |
| WO | WO 93/00360 | 1/1993 |
| WO | WO 93/04713 | 3/1993 |
| WO | WO 93/08829 | 5/1993 |
| WO | WO 93/14110 | 7/1993 |
| WO | WO 93/16185 | 8/1993 |
| WO | 9415951 A1 | 7/1994 |
| WO | WO 95/19181 | 7/1995 |
| WO | WO 95/23865 | 9/1995 |
| WO | 9602577 A1 | 2/1996 |
| WO | WO 96/27011 | 9/1996 |
| WO | WO 96/30046 | 10/1996 |
| WO | WO 96/40210 | 12/1996 |
| WO | WO 97/26912 | 7/1997 |
| WO | WO 98/06248 | 2/1998 |
| WO | WO 98/23761 | 6/1998 |
| WO | WO 98/45331 | 10/1998 |
| WO | WO 98/51793 | 11/1998 |
| WO | WO 99/01556 | 1/1999 |
| WO | 0012618 A1 | 3/2000 |
| WO | WO 00/46262 | 8/2000 |
| WO | 0067901 A1 | 11/2000 |
| WO | WO 00/75348 | 12/2000 |
| WO | WO 01/40309 | 6/2001 |
| WO | 2004/092393 A1 | 10/2004 |
| WO | WO 2005/010141 | 2/2005 |
| WO | 2005/021129 A1 | 3/2005 |
| WO | WO 2006/085321 | 8/2006 |
| WO | 2007/002690 A2 | 1/2007 |
| WO | 2007038523 A1 | 4/2007 |
| WO | 2007/073311 A1 | 6/2007 |
| WO | 2007104456 A1 | 9/2007 |
| WO | 2007148230 A1 | 12/2007 |
| WO | 2008004988 A1 | 1/2008 |
| WO | WO 2008 079280 | 7/2008 |
| WO | 2008097154 A1 | 8/2008 |
| WO | 2009089570 A1 | 7/2009 |
| WO | 2009141664 A1 | 11/2009 |
| WO | 2009158606 A1 | 12/2009 |
| WO | 2010/082894 A1 | 7/2010 |

OTHER PUBLICATIONS

Gupta et al., "Affinity precipitation of proteins", Journal of Molecular Recognition, vol. 9, No. 5-6 1996, pp. 356-359.
Carter et al, Proc.National Acad. Sci. USA, 89:4285-4289 (1992).
St. John et al., Chest, 103:943 (1993).
Kim et al., Growth Factors, 7:53-64 (1992).
Stoppa et al., Transplant Intl. 4:3-7 (1991).
Hourmant et al, Transplantation 58:377-380 (1994).
Presta et al., J Immunol 151:(5)2623-2632 (1993).
Lorenz et al., J. Immunol 156(4):1646-1653 (1996).
Dhainaut et al. Crit Care Med. 23(9):1461-1469 (1995).
Choy et al. Arthritis Rheum 39(1):52-56 (1996).
Reichmann et al. Nature 332:323-327(1) (1998).
Graziano et al. J. Immunol 155(10):4996-5002 (1995).
Sharkey et al., Cancer Res. 55(23Suppl):5935s-5945s (1995).
Ceriani et al., Cancer Res. 55(23): 5852s-5856s (1995).
Richman et al., Cancer Res. 55(23) Supp): 5916s-5920s (1995).
Litton et al., Eur J. Immunol 26(1):1-9 (1996).
Ellis et al., J Immunol. 155(2):925-937 (1995).
Jurcic et al., Cancer Res. 55(23 Suppl):5908s-5910s (1995).
Juweid et al., Cancer Res 55(23 Suppl):5899s-5907s (1995).
Kohler et al., Nature 256:495-497 (1975).
Goding, Monoclonal Antibodies: Principles and Practice, pp. 59-103 (Academic Press 1986).
Kozbor, J. Immunol., 133:3001 (1984).
Brodeur et al., Monoclonal Antibody Production Techniques and Applications, pp. 51-63 (Marcel Dakker, Inc., New York 1987).
Morrison, et al., Proc.Natl.Acad. Sci. USA, 81:6651 (1984).
McCafferty et al., Nature, 348:552-554 (1990).
Clackson et al., Nature 352:624-628 (1991).
Marks et al., Bio/Technology, 10:779-783 (1992).
Waterhouse et al., NucAcids Res., 21_2265-2266 (1993).
Jones et al., Nature, 321:522-525 (1986).
Verhoeyen et al., Science 239:1534-1536 (1988).
Jokobovits et al., Proc. Natl.,Acad.Sci. USA 90:2551 (1993).
Jakobovits et al., Nature 362:255-258 (1993).
Bruggermann et al., Year in Immuno., 7:33 (1993).
Duchosal et al., Nature 355:258 (1992).
Hoogenboom et al., J. Mol.Bio., 227:381 (1992).
Vaughan et al., Nature Biotech 14:309 (1996).
Morimoto et al., Journal of Biochemical an Biophysical Methods 24:107-117 (1992).
Brennan et al., Science, 229:81 (1985).
Millstein et al., nature, 305:537-539 (1983).
Traunecker et al., EMBO J., 10:3655-3659 (1991).
Shalaby et al., J. Exp.Med., 175:217-225 (1992).
Kostelny et al., J. Immunol., 148(5):1547-1533 (1992).
Hollinger et al., Proc. Natl.Acad. Sci. USA 90:6444-6448, (1993).
Gruber et al., J. Immunol., 152:5368 (1994).
Zapata et al., Protein Eng. 8(10):1057-1062 (1995).
Tutt et al., J. Immunol. 147:60 (1996).
Hoogenboom et al., Mol.Immunol. 28:1027-1037 (1991).
Aruffo et al., Cell 61:1303-1313 (1990).
Stamenkovic et al., Cell 66:1133-1144 (1991).
Chen et al., A new temperature-and pH-responsive copolymer for possible use in protein cojugation, Macromol. Chem. Phys., 196:1251-1259 (1995).

Chen et al., Polymer-protein conjugates, Biomaterials 11:631-633 (1990).
Guoqiang et al., Alternative modes of precipitation of Eudragit S 100: a potential ligand carrier for affinity precipitation of protein, Biseparation 5:339-350 (1995).
Saitoh, et al., Concentration of Hydrophobic Organic Compounds by Polymer-Mediated Extraction, Anal. Chem. 71(20): 4506-4512 (1999).
Ayano et al., Aqueous chromatography system using pH-and temperature-responsive stationary phase with ion-exchange groups, J. Chromotagraphy A, 1119:58-65 (2006).
Kanazawa et al., Temperature-responsive stationary phase utilizing a polymer of proline derivative for hydrophobic interaction chromatography using an aqueous mobile phase, J. Chromatography A 1106: 152-258 (2006).
Temperature-responsive liquid chromatography, Anal. Chem. 69(5):823-830 (1997).
Schmaljohann, Thermo-and pH-responsive polymers in a drug delivery, Adv. Drug Delivery Reviews 58:1655-1670 (2006).
Suedee et al., Termperature sensitive dopamine-imprinted (N,N-methyline-bis-acrylamide cross-linked) polymer and its potential application to the selective extraction of adrenergic drugs from urine, J. Chromotagr.A 1114:239-249 (2006).
CellSeed Inc.: Technology, Website, Temperature-responsive polymer, Jan. 29, 2008. http://cellseed.com/technology-e/index/html.
Sims, et al., J. Immunol 151:2296 (1993).
Carter et al., Bio/Technology 10:163-167 (1992).
International Search Report, PCT/US2007/20640, 3 pgs. Feb. 13, 2008.
Hilbrig, F. et al. J Chroma 790:79-90 Jun. 2003.
Dainaik, M et al. Biioseparation 7(4-5):231-240 Jul. 1998.
Kumar, A et al. Biotechnology and Bioengineering 75(5):570-580 Dec. 5, 2001.
Senstad, C et al. Biotehnology and Bioengineering 34(3):387-393 Mar. 1989.
Nature, vol. 373, 5, Jan. 5, 1995, pp. 49-52; Guohua Chen et al.; "Graft copolymers that exhibit temperature-induced phase transitions over a wide range of pH".
Nature, vol. 411, May 3, 2001, pp. 59-62; Zhongli Ding et al.; "Size-dependent control of the binding of biotinylated proteins to streptavidin using a polymer shield".
Journal of Chromatography A, 1195 (2008),pp. 94-100; I. Filipa Ferreira et al.; "Purification of human immunoglobulin G by thermoseparating aqueous two-phase systems".
Bioconjugate Chem. 1999, 10, pp. 720-725; Robin B. Fong et al.; Thermoprecipitation of Streptavidin via Oligonucleotide-Mediated Self-Assembly with Poly(N-isopropylacrylaminde).
BioTechnology and BioEngineering, vol. 79, No. 3, Aug. 5, 2002, pp. 271-276; Robin B. Fong et al.; "Affinity Separation Using an Fv Antibody Fragment-"Smart" Polymer Conjugate".
Chimia 55, No. 3, 2001, pp. 196-200; Ruth Freitag et al.; "Stimulus-Responsive Polymers for Bioseparation".
BioTechnology and BioEngineering, vol. 71, No. 3, 2000/2001; Frederic Garret-Flaudy et al.; Use of the Avidin (Imino) biotin System as a General Approach to Affinity Precipitation.
BioTechnology and BioEngineering, vol. 60, No. 5, Dec. 5, 1998; Kazuhiro Hoshino et al.; "Preparation of a New Thermo-Responsive Adsorbent with Maltose as a Ligand and Its Application to Affinity Precipitation".
BioTechnology and BioEngineering, vol. 75, No. 5, Dec. 5, 2001; A. Kumar et al.; "Type-Specific Separation of Animal Cells in Aqueous Two-Phase Systems Using Antibody Conjugates with Temperature-Sensitive Polymers".
Prog. Polym. Sci. 32 (2007), pp. 1205-1237; Ashok Kumar et al.; "Smart Polymers: Physical forms and bioengineering applications".
Bioconjugate Chem., vol. 14, No. 3, 2003, pp. 575-580; Noah Malmstadt et al.; "Affinity Thermoprecipitation and Recovery of Biotinylated Biomolecules via a Mutant Streptavidin-Smart Polymer Conjugate".
Analytical Chemistry, vol. 75, No. 13, Jul. 1, 2003, pp. 2943-2949; Noah Malmstadt et al.; "A Smart Microfluidic Affinity Chromatography Matrix Composed of Poly(N-isopropylacrylamide)-Coated Beads".
Process Technology Proceedings, 4, Jul. 28-Aug. 1, 1986, pp. 429 & 441; Yosry A. Attia; "Flocculation in Biotechnology and Separation Systems".
Innovative Food Science and Emerging Technologies, 2007, pp. 1-11; Pankaj Maharjan et al.; "Novel chromatographic separation—The potential of smart polymers".
Colloids and Surfaces B: Biointerfaces 6, 1996, p. 27-49; C.S. Chern et al.; "Characterization of pH-sensitive polymeric supports for selective precipitation of proteins".
Journal of Biotechnology 49, 1996, pp. 173-178; Jian-guo Shan et al.; "Flocculation of cell, cell debris and soluble protein with methacryloyloxyethyl trimethylammonium chloride-acrylonitrile copolymer".
Separation Science and Technology, 37(I), pp. 217-228, 2002; J. Yu et al.; "Selective Precipitation of Water-Soluble Proteins Using Designed Polyelectrolyte".
Isolation and Purification of Proteins 2003; Kumar et al.—edited by Rajni Hatti-Kaul et al.
Office Action dated Jun. 11, 2010 in corresponding U.S. Appl. No. 12/004,319.
International Search Report dated Apr. 24, 2008 in corresponding PCT/US07/26090.
International Search Report dated Aug. 27, 2009 in corresponding PCT/US08/013736.
J.Mol.Biol. (1991) 222, 581-597, James D. Marks et al.; "By-passing Immunization Human Antibodies from V-gene Libraries Displayed on Phage".
Flocculation in Biotechnology and Separation Systems, 1987, pp. 441-455; L.B. Eriksson et al.; "Flocculation of E.Coli Bacteria With Cationic Polyelectrolytes".
Flocculation in Biotechnology and Separation Systems, 1987, pp. 457-466; Ingalill Persson et al.; "Flocculation of Cell Debris For Improved Separation Configuration".
Am Chem Society, 1988, Chapter 7, pp. 72-101,"Scale-Up of Bioseparations for Microbial and Biochemical Technology", Ladisch, et al.
Biotech. Progress, 2008, V24, No. 3, pp. 488-495, "Advances in Primary Recovery: Centrifugation and Membrane Technology", Roush, et al.
Am Inst. of Chem Engineers, Journal, Jul. 2003, vol. 49, No. 7, pp. 1687-1701, "Flocculation of Biological Cells: Experiment vs. Theory", Han, et al.
Biochem Eng. Journal, 40, (2008) pp. 512-519, "Flocculation enhanced microfiltration of Escherichia coli lysate", Karim, et al.
Biotechnology Techniques, vol. 4, No. 1, pp. 55-60, (1990), "The Flocculation of Bacteria Using Cationic Synthetic Flocculants and Chitosan", Hughes, et al.
Biotechnology and Bioengineering, vol. 108, No. 1, Jan. 2011, pp. 50-58, "Effects of Solution environment on Mammalian Cell Fermentation Broth Properties: Enhanced Impurity Removal and Clarification Performance", Westoby, et al.
Biotechnology and Bioengineering, vol. 86, No. 6 (2004), pp. 612-621, "Clearance of Minute Virus of Mice by Flocculation and Microfiltration", Wickramasinghe, et al.
Journal of Biotechnology, 49 (1996) pp. 173-178, "Flocculation of cell, cell debris and soluble protein with methacryloyloxyethyl trimethylammonium chloride-acrylonitrile copolymer", Shan, et al.
Journal of Biotechnology, 128, (2007), pp. 813-823, "The use of chitosan as a flocculant in mammalian cell culture dramatically improves clarification throughput without adversely impacting monoclonal antibody recovery", Riske, et al.
Journal of Membrane Science, 182, (2001), pp. 161-172, "Flocculation to enhance microfiltration", Kim, et al.
Am Inst of Chem Engineers, V 26, No. 5, (2010), pp. 1322-1331, "Monoclonal Antibody Purification Using Cationic Polyelectrolytes: An Alternative to Column Chromatography", Peram, et al.
Journal of Chromatography, 8, 878 (2010) pp. 798-806, "Using precipitation by polyamines as an alternative to chromatographic separation in antibody purification processes", Ma, et al.
Desalination, 147, (2002), pp. 25-30, "Enhanced microfiltration of yeast by flocculation", Wickramasinghe, et al.

J Phys. Chem. B (2007), V111, pp. 8649-8654, "Cationic Flocculants Carrying Hydrophobic Functionalities: Applications for Solid/Liquid Separation", Schwarz, et al.

Langmuir, 2005, 21, pp. 11673-11677, "pH-Dependence of the Properties of Hydrophobically Modified Polyvinylamine", Chen, et al.

Russian Chemical Reviews (1995), 64(5), pp. 471-489, ";Smart' polymers in biotechnology and medicine", Galaev.

Bioseparation 7: pp. 207-220 (1999), "Polycomplexes—potential for bioseparation", Izumrudov, et al.

Biotechnology and Bioengineering (1998), vol. 59, Issue 6, pp. 695-704, "Affinity Precipitation of Amylase Inhibitor from Wheat Meal by metal Chelate Affinity Binding Using Cu(II)-Loaded Copolymers of 1-Vinylimidazole with N-Isopropylacrylamide", Kumar, et al.

Biotechnology and Bioengineering (1998), V 60, Issue 5, pp. 568-579, "Preparation of a New Thermo-Responsive Adsorbent with Maltose as a Ligand and Its Application to Affinity Precipitation", Hoshino, et al.

Analyst, 2004, 129, pp. 421-427, "Capturing of acidic macromolecules from biological samples using a temperature-responsive polymer modified with poly-L-lysine", Hayashi, et al.

AIChE Journal, Aug. 2009, vol. 55, No. 8, pp. 2070-2080, "Effect of Molecular Weight of Poly(N-isopropylacrylamide) Temperature-Sensitive Flocculants on Dewatering", Li, et al.

Kona, No. 20 (2002) pp. 246-250, "Flocculation Mechanism of Suspended Particles Using the Hydrophilic/Hydrophobic Transition of a Thermosensitive Polymer", Sakohara, et al.

Journal of Biotechnology, 49 (1996), pp. 189-199, "Evaluation of affinity precipitation and a traditional affinity chromatographic precedure for purification of soybean lectin, from extracts of soya flour", Larsson, et al.

Macromolecular Bioscience, 2005, 5, pp. 373-378, "Highly Branched Stimuli Responsive Poly[(N-isopropylacrylamide)-co-(1,2-propandiol-3-methacrylate)]s with Protein Binding Functionality", Carter, et al.

Journal of Chromatography B, 761 (2001), pp. 247-254, "New antibody purification procedure using a thermally responsive poly(N-isopropylacrylamide)-dextran derivative conjugate", Anastase-Ravion, et al.

Process Biochemistry 34 (1999), pp. 577-580, "Purification of Aspergillus sp xylanase by precipitation with an anionic polymer Eudragit S 100", Gawande, et al.

Journal of Colloid and Interface Science, 179, pp. 188-193 (1996), Art. No. 0201, "Temperature-Sensitive Flocculants Based on Poly (N-isopropylacrylamide-co-diallyldimethylammonium Chloride)", Deng, et al.

The Affinity Precipitation Thesis (Aug. 2007), pp. 1-130, Stocker-Majd, et al, submitted in 2 parts: "Affinity-1" and "Affinity 2".

Biotechnology and Bioengineering, vol. 40, pp. 1381-1387, (1992), "Purification of recombinant protein A by aqueous two-phase extraction integrated with affinity precipitation", Kamihira, et al.

Office Action dated Jun. 21, 2011 in corresponding U.S. Appl. No. 12/316,708.

Final Rejection dated Apr. 13, 2011 in corresponding U.S. Appl. No. 12/004,319.

Office Action mailed Oct. 3, 2011 copending U.S. Appl. No. 12/004,319.

Trends in Biotechnology, Jun. 1991, vol. 9 (6), pp. 191-196, "Application of reversibly soluble polymers in bioprocessing", Fujii, et al.

Trend in Biotechnology, Aug. 1999, vol. 17 (8), pp. 335-340, "'Smart' polymers and what they could do in biotechnology and medicine", Galaev, et al.

Office Action-Restriction-mailed Feb. 7, 2012 in co-pending U.S. Appl. No. 121/448,004.

* cited by examiner

PURIFICATION OF PROTEINS

This application claims priority of U.S. Provisional Application Ser. No. 60/876,330 filed Dec. 21, 2006, the disclosure of which is incorporated herein by reference.

The present invention relates to the purification of biomolecules. More particularly, it relates to the purification of biomolecules such as proteins, polypeptides, antibodies and the like, by a solubilized polymer to remove impurities from a solution/suspension by a controlled precipitation mechanism.

BACKGROUND OF THE INVENTION

The general process for the manufacture of biomolecules, such as proteins, particularly recombinant proteins typically involves two main steps: (1) the expression of the protein in a host cell, followed by (2) the purification of the protein. The first step involves growing the desired host cell in a bioreactor to effect the expression of the protein, Some examples of cell lines used for this purpose include Chinese hamster ovary (CHO) cells, myeloma (NSO) cells, bacterial cells such as e-coli and insect cells. Once the protein is expressed at the desired levels, the protein is removed from the host cell and harvested. In some instances the protein has been expressed outside of the cell and in others it is still within the cell that must be lysed to allow one access to the protein of interest. Suspended particulates, such as cells, cell fragments, lipids and other insoluble matter are typically removed from the protein-containing fluid by filtration or centrifugation, resulting in a clarified fluid containing the protein of interest in solution as well as other soluble impurities.

The second step involves the purification of the harvested protein to remove impurities which are inherent to the process. Examples of impurities include host cell proteins (HCP, proteins other than the desired or targeted protein), nucleic acids, endotoxins, viruses, protein variants and protein aggregates.

This purification typically involves several chromatography steps, which can include affinity, ion exchange hydrophobic interaction, etc. One example of chromatography process train for the purification of proteins involves protein-A affinity, followed by cation exchange, followed by anion exchange. The protein-A column captures the protein of interest or target protein by an affinity mechanism while the bulk of the impurities pass through the column to be discarded. The protein then is recovered by elution from the column. Since most of the proteins of interest have isoelectric points (pI) in the basic range (8-9) and therefore being positively charged under normal processing conditions (pH below the pI of the protein), they are bound to the cation exchange resin in the second column. Other positively charged impurities are also bound to this resin. The protein of interest is then recovered by elution from this column under conditions (pH, salt concentration) in which the protein elutes while the impurities remain bound to the resin. The anion exchange column is typically operated in a flow through mode, such that any negatively charged impurities are bound to the resin while the positively charged protein of interest is recovered in the flow through stream. This process results in a highly purified and concentrated protein solution.

Other alternative methods for purifying proteins have been investigated in recent years, one such method involves a flocculation technique. In this technique, a soluble polyelectrolyte is added to a clarified or unclarified cell culture broth to capture the impurities thereby forming a flocculant, which is allowed to settle and can be subsequently removed from the protein solution.

The main drawback of this flocculation technique is that it requires that the polyelectrolyte be added in the exact amount needed to remove the impurities. If too little flocculent is added, impurities will remain in the protein solution and if too much flocculent is added, the excess polyelectrolyte needs to be removed from the resulting solution. The exact level of impurities in the broth is extremely difficult to predict due to the relatively large degree of variability in the process (from batch to batch) as well as the vast differences between processes to produce different proteins. Removing any excess polyelectrolyte is practically impossible because it is a soluble material and thus it is carried through the process as an undesirable impurity.

What is needed is a better process for purifying biomolecules.

SUMMARY OF THE INVENTION

The present invention relates to a selectively soluble polymer capable of binding to one or more constituents in a biological material containing stream and the methods of using such a material to purify a biomolecule from such a stream.

In the following description, the term polymer shall mean a polymer capable of binding to one or more constituents in a biological material containing stream unless otherwise stated.

The terms selected biomolecule, target biomolecule or molecule, target protein, biomolecule or protein of interest, or similar terms all refer to products of a biomolecule manufacturing process.

The polymer is soluble in an aqueous based solvent under a certain set of process conditions such as pH or temperature or salt concentration or the like and is rendered insoluble and precipitates out of solution upon a change in conditions (temperature, pH, salt or the like). While in its solubilized state, the polymer is capable of binding to a selected entity within the stream such as impurities (cells, cell fragments, lipids, DNA, RNA, host cell protein, endotoxins, virus, etc) in a cell broth and remains capable of binding to that entity even after the polymer is precipitated out of solution. The precipitate can then be easily removed, such as by being filtered out from the remainder of the stream and the desired biomolecule is recovered and further processed.

The polymer being bound to one or more impurities, it can either be disposed of or the one or more impurities can be eluted from the polymer and the polymer is then cleaned or sanitized and reused if desired. It can also be washed to ensure that any biomolecules of interest have been recovered for further use or processing.

It is an object of the present invention to provide a polymer that is capable of being selectively solubilized in a liquid under certain conditions and to be insoluble and to precipitate out of solution under different conditions in that liquid.

It is another object of the present invention to provide a polymer that is capable of being selectively solubilized in a liquid under certain conditions and to be insoluble and to precipitate out of solution under different conditions in that liquid and to allow any excess polymer in solution to be recovered from the solution by precipitation.

It is a further object of the present invention to provide a polymer that is capable of being solubilized under a first certain set of conditions in the liquid and to be capable of binding to one or more entities either in the liquid while in its solubilized form and/or to retain the one or more entities or bind to the impurities or have the impurities bind to it as/after being precipitated from the liquid under different conditions in the liquid.

It is another object of the present invention to provide a polymer capable of being solubilized under certain ranges of pH, temperature, temperature and salt concentration or the like and to have it bind to one or more entities either in the liquid while in its solubilized form and/or to retain the one or more entities or bind to the impurities or have the impurities bind to it as/after being precipitated under a different set of ranges of pH, temperature, temperature and salt concentration or the like.

It is a further object of the present invention to provide a process for purifying a selected biomolecule from a biomolecule containing stream by either having the stream at a given condition or modifying the stream to a given condition and adding a polymer soluble in the stream at that given condition, allowing the solubilized polymer to circulate throughout the stream, further changing the given condition of the stream so as to cause the polymer to become insoluble in the stream and precipitate out with one or more entities of the stream, separating the stream from the polymer and processing one or both further.

It is an object to use one or more polymers such as poly(N-vinyl caprolactam), poly(N-acryloylpiperidine), poly(N-vinylisobutyramide), poly (N-substituted acrylamide) including [poly(N-isopropylacrylamide), poly(N,N'-diethylacrylamide), and poly(N-acryloyl-N'-alkylpiperazine)], hydroxyalkylcellulose, copolymers of acrylic acid and methacrylic acid or methacrylic acid and methyl methacrylate, polymers and copolymers of 2 or 4-vinylpyridine and chitosan to selectively remove one or more impurities from a stream containing impurities along with a desired biomolecule.

It is an object to do the process with an overabundance of polymer and recover substantially all of the polymer as a precipitate from the mixture.

It is an additional object of the present invention to provide the process based on a polymer which is soluble based upon a condition selected from temperature, temperature and salt content or pH.

It is another object of the present invention to provide a polymer selected from N-isopropylacrylamide-containing polymers, functionalized agarose, functionalized polyethylene oxide, cationic and anionic polyelectrolytes.

It is a further object of the present invention to provide a process for purifying a selected biomolecule from a biomolecule containing mixture by setting the mixture to a given condition, modifying a carrier liquid compatible with the mixture to the same given condition, adding a polymer soluble in the carrier liquid at that given condition to the carrier liquid, allowing the carrier liquid with the solubilized polymer to the mixture and allowing it to circulate throughout the mixture, changing the given condition of the stream so as to cause the polymer to become insoluble in the stream and precipitate out along with one or more entities of the mixture, separating the mixture from the polymer and processing one or both further.

It is an additional object of the present invention to provide a static mixer for causing the mixture and solubilized polymer to mix and to allow the polymer to bind to the one or more entities.

It is another object of the present invention to provide that the one or more entities are impurities in the mixture.

It is a further object of the present invention to provide that the one or more entities are impurities in the mixture selected from host cell protein, cells, cell fragments, nucleic acids and endotoxins.

It is an object of the present invention to provide that the one or more entities are viruses which are either removed or rendered inactive by the polymer process. For example, viruses may be removed by the precipitated polymer or they may be rendered inactive by the polymer itself or by the conditions under which the polymer is dissolved into the mixture or rendered insoluble from the mixture.

It is an additional object of the present invention to provide a process for the purification of a mixture of biological constituents in a single step.

It is another object of the present invention to provide a process for the purification of a mixture of biological constituents selected from proteins, polypeptides, monoclonal antibodies, humanized, chimeral or animal monoclonal antibodies polyclonal antibodies, antibody fragments, multispecific antibodies, immunoadhesins, and $C_H2/C_H3$ region-containing proteins.

It is a further object of the present invention to provide a process of having a mixture containing a biomolecule of interest at a set range of conditions that will cause one or more polymers of choice to go into solution, adding the one or more polymers and having one or more polymers go into solution, mixing the one or more polymers with entities of the mixture, changing the conditions of the mixture to cause the one or more polymers to precipitate out of solution while retaining one or more entities of the mixture and then separating the precipitate from the remainder of the mixture.

It is a further object of the present invention to provide a carrier liquid for the polymer having conditions suitable to cause the polymer to go into solution in the carrier liquid and then to add the carrier liquid with the dissolved polymer to the mixture.

It is an additional object of the present invention to provide one or more static mixers to mix the polymer and the mixture.

It is another object of the present invention to provide a process for recovering a biomolecule of interest directly from a fermentor or bioreactor in which it has been made.

It is a further object of the present invention to provide a process for recovering a biomolecule of interest from a mixture obtained from a fermentor or bioreactor in which it has been made.

It is an additional object of the present invention to provide a filtration step to separate the precipitate from the remainder of the mixture.

It is another object of the present invention to provide a normal flow filtration step to separate the precipitate from the remainder of the mixture.

It is a further object of the present invention to provide a tangential flow filtration step to separate the precipitate from the remainder of the mixture.

It is an additional object of the present invention to provide a centrifugation step to separate the precipitate from the remainder of the mixture.

It is another object of the present invention to provide a decantation step to separate the precipitate from the remainder of the mixture.

It is an additional object of the present invention to provide a further step to recover the one or more constituents of the mixture from the precipitated polymer.

It is a further object of the present invention to provide additional processing to the biomolecule of interest.

It is an additional object of the present invention to provide a further step of formulating the biomolecule in a pharmaceutically acceptable carrier and using it for various diagnostic, therapeutic or other uses known for such biomolecules.

It is an object of the present invention to provide a purified biomolecule in one step, directly out of the bioreactor with no further processing required.

It is an additional object of the present invention to improve the efficiency of the clarification (centrifuge or prefiltration) step so that the clarifier (centrifuge or prefilter) exhibits enhanced throughput or capacity.

It is another object of the present invention to improve the efficiency of the clarification (centrifuge or prefiltration) step so that the resulting clarified mixture is "cleaner" (going into the sterile membrane filtration step) than a conventional process in which the precipitation technique has not been effected.

It is an additional object of the present invention to improve the efficiency of the sterile membrane filtration step so that the membrane filter exhibits enhanced throughput (capacity).

It is an additional object of the present invention to provide a purified mixture which enables the improved cleanabiliity of membrane filters and/or chromatography resins that may be used in additional processing following the precipitation step.

It is a further object of the present invention to compress the additional processing steps into one continuous process.

It is an additional object of the present invention to effect the purification and recovery of a target molecule with additional processing but without the need for bind and elute chromatography steps.

It is a further object of the present invention to effect the purification and recovery of a target molecule with additional processing but without the need for any chromatography steps.

It is a further object of the present invention to effect the purification and recovery of a target molecule with additional processing in a flow through mode.

It is a further object of the present invention to effect the purification and recovery of a target molecule with additional processing using membrane adsorbers.

It is a further object of the present invention to effect the purification and recovery of a target molecule with additional processing using a disposable process.

It is a further object of the present invention to effect virus inactivation as part of the precipitation process.

It is a further object of the present invention to use a UF step to concentrate the target protein after it has been purified and recovered with the precipitation technique.

It is an additional object of the present invention to effect the purification and recovery of a target molecule with additional processing using an enhanced UF (charged UF) process.

IN THE DRAWINGS

Figure 6A:
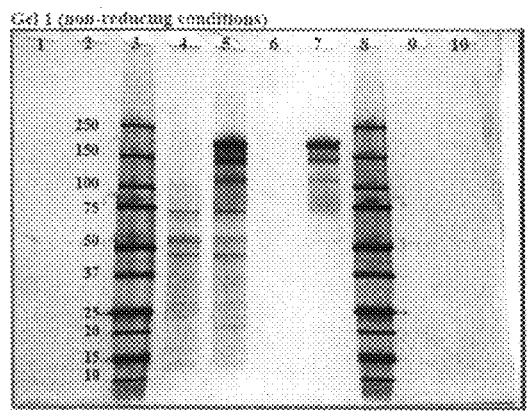

FIGS. 6A and B show gel electrophoresis data of Example 11 according to the present invention.

Figure 7:
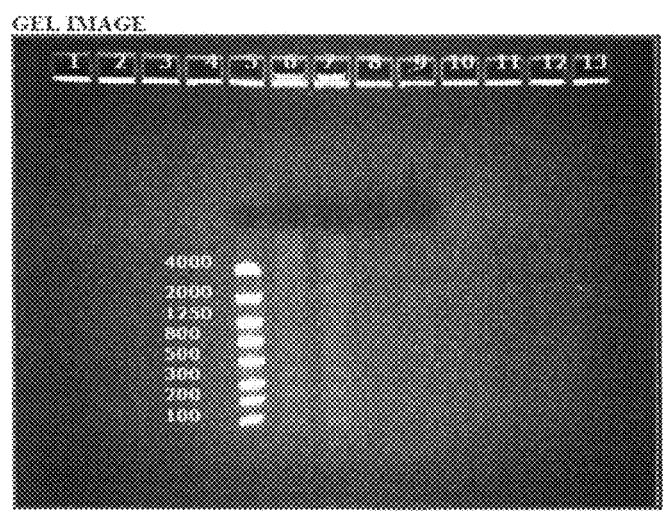

FIG. 7 shows SDS-PAGE data of Example 11 according to the present invention.

DETAILED DESCRIPTION OF THE INVENTION

The invention is to use a liquid phase or solubilized polymer that has a capability, such as affinity or charge or hydrophobicity and the like, to remove undesirable soluble and suspended impurities from a fluid containing a desirable biomolecule of interest. Preferred polymers have an affinity or electrostatic ability. The biomolecule of interest is then recovered and further processed as desired or required.

More specifically, the idea relates to the process of using one or more polymers soluble in a liquid phase to remove impurities from a solution/suspension by a precipitation mechanism and which polymer can also be removed, if present, in any excess, by the same mechanism. By way of example, this idea can best be described in the context of protein purification although it can be used to purify any solute from complex mixtures as long as the mechanism of removal applies to the specific solute of interest.

The one or more polymers can be used in excess unlike flocculants and can be recovered essentially completely from the mixture by the precipitation action. This allows one to operate the purification step with greater windows of use and without having to calculate the precise amount of material that needs to be used.

The present concept is based on the fact that certain polymers undergo changes in properties as a result of changes in the environment in which they are in. The most common polymer property to change as a result of a stimulus is solubility and the most common stimuli are temperature salt concentration and pH. As an example, a polymer may remain in solution as long as the pH, salt or temperature is maintained within a certain range but it will precipitate out of solution as soon as the pH, salt or temperature is raised or lowered outside of said range.

Certain polymers, such as poly (N-isopropylacrylamide), agarose, polyethylene oxide, etc. are examples of polymers that exhibit solubility changes as a result of changes in temperature. Other polymers, such as certain catonic and anionic polyelectrolytes, especially poly(4-vinylpyridine), poly(2-vinylpyridine), copolymers of 4-vinyl pyridine or 2-vinyl pyridine with other monomers such as styrene, butyl methacrylate, etc., chitosan and copolymers of acrylic acid or methacrylic acid with other monomers such as methyl methacrylate are examples of polymers that exhibit changes in solubility as a result of changes in pH and/or salt concentration.

The precise mechanism is not currently known. It may be that the polymer(s) interact with the entity or entities while in a soluble state and continue to bind to them upon precipitation. It may also be that the polymer and/or entity(s) bind to one another as the polymer is in the process of precipitating. It may be another mechanism as yet unknown to the inventor at this time. The inventor does not wish to be bound to any particular theory of what mechanism is being used but that the invention encompasses any all such mechanisms and phenomena.

Depending upon the polymer used, the process used can vary. However, the processes will generally involve having one or more conditions of the liquid or the mixture, such as a cell broth, at the correct pH, temperature, temperature and salt concentration or other condition used to cause the polymer(s) to become soluble and then adding the polymer(s) either directly or already solubilized in a carrier liquid, such as water, to the mixture. In many instances the mixture will be at the proper condition to allow the polymer(s) to be simply added to the mixture. In other instances, the mixture may need to be conditioned or modified to be at the desired condition. This modification or conditioning can be by modifying the mixture first and then adding the polymer(s), by adding the polymer(s) to a carrier liquid that is conditioned to the desired state and simply adding it to the mixture such that the carrier liquid is sufficient to cause the mixture to thus reach that condition or to do both. The mixture and the solubilized or soluble polymer(s) are then mixed to ensure the polymer(s) is solubilized, and that the entities of the mixture and the solubilized polymer(s) have sufficient and intimate contact with each other. The conditions of the liquid in the mixture are then changed (pH, temperature, salt content, combinations thereof, etc) that causes the polymer(s) to become insoluble and precipitate out of the mixture as a solid while either still remaining bound to the one or more entities it contacted while soluble in the mixture or to bind to the entities as it precipitates and continue to bind to it thereafter. The precipitate and remaining mixture are then separated such as by centrifugation or filtration or gravity and time with the liquid portion being decanted. Depending on what was bound to the precipitate, it is either disposed of (if it bound to impurities) or treated (such as by elution and or washing) one or more times to remove any residual impurities or contaminants and then sanitized for reuse.

One polymer or a blend of polymers may be used in the present invention and it is meant to cover both embodiments whenever the term polymer, polymer(s) or one or more polymers is used hereafter.

As discussed above the polymer may be added directly to the conditioned mixture. Alternatively, it can be added to a carrier liquid in which it is soluble and which carrier preferably is also compatible with the mixture. One such carrier liquid is water, water adjusted to the correct pH by the addition of acids or bases, another is an aqueous based solution such as saline, buffered solutions or blends of water with an organic solvent such as alcohol. The selection of carrier liquid is dependent on the mixture to which it is added as to what is preferred and tolerated. The polymer is added to the carrier liquid that either has already been conditioned (such as pH adjusted or heated to a desired temperature or heated to a desired temperature with the addition of one or more salts or cooled to the desired temperature with or without one or more salts) or it can be added and then the carrier is conditioned to cause the solubilizing of the polymer in the carrier. The carrier/soluble polymer blend is then added to the mixture.

The mixture may be contained in a mixing vessel such as a tapered bottom metal (preferably stainless steel more preferably 304 or 316L stainless steel) or glass vat or tank. Alternatively, especially when a cell culture or microbial or yeast culture is used, it may be the bioreactor or fermentor in which it has been grown. It may also be a disposable bioreactor or fermentor or a disposable mixing bag such as a plastic bag as is available from Millipore Corporation of Billerica, Mass. The mixture and polymer are brought into intimate contact through a mixing action that may be done by a magnetic stirred bar, a magnetic driven mixer such as a NovAseptic® mixer available from Millipore Corporation of Billerica Mass., a Lightning-type mixer, a recirculation pump, or a rocking motion closed mixing bag or bioreactor or fermentor, such as is shown in US 2005/0063259A1 or an airlift type of mixer or reactor in which rising bubbles in the liquid cause a circulatory pattern to be formed.

Alternatively, the mixture and polymer (either by itself or in a carrier) can be in separate containers and mixed in line in a static blender. The blend can either then go to a container or to a centrifuge or a filter where the polymer is caused to precipitate and the precipitated polymer and its bound one or more entities is separated from the remainder of the mixture. Then at least the remainder of the mixture is further processed.

In another embodiment, the mixture and polymer (either by itself or in a carrier) are blended together in the container holding the mixture and further mixed in line in a static blender. The blend is then treated to cause precipitation of the polymer and its bound entity(s). It can either then go to a container or to a centrifuge or to a filter where the precipitated polymer and its bound one or more entities is separated from the remainder of the mixture. Then at least the filtrate is further processed.

Using centrifugation, one can easily and quickly separate the precipitated polymer from the remainder of the liquid mixture. After centrifugation, the supernatant, generally the remainder of the mixture is drawn off. Either the drawn off mixture or the precipitated polymer or both if desired is further processed.

Simple settling of the precipitated solids and decantation of the supernatant fluid may also be used if desired.

Filtration can be accomplished in a variety of manners. Depending upon the size of the polymer as it is precipitated; one may use one or more filters of varying sizes or asymmetries.

The selection of type and size of filter will depend on the volume of precipitate to be captured and whether one wishes to further process the precipitated polymer or just the remainder of the mixture, Membrane based filters, preferably microporous membranes can be used in the present invention. Such filters are generally polymeric in nature and can be made from polymers such as but not limited to olefins such as polyethylene including ultrahigh molecular weight polyethylene, polypropylene, EVA copolymers and alpha olefins, metallocene olefinic polymers, PFA, MFA, PTFE, polycarbonates, vinyl copolymers such as PVC, polyamides such as nylon, polyesters, cellulose, cellulose acetate, regenerated cellulose, cellulose composites, polysulfone, polyethersulfone, polyarylsulfone, polyphenylsulfone, polyacrylonitrile, polyvinylidene fluoride (PVDF), and blends thereof. The membrane selected depends upon the application, desired filtration characteristics, particle type and size to be filtered and the flow desired. Preferred membrane based filters include DURAPORE® PVDF membranes available from Millipore Corporation of Billerica Mass., MILLIPORE EXPRESS® and MILLIPORE EXPRESS® PLUS or SH_PES membranes available from Millipore Corporation of Billerica Mass.

Depending on the mixture, polymer and the nature of component(s) being removed the membrane may be hydrophilic or hydrophobic. Preferred membranes are hydrophilic and are low in protein binding.

The membrane may be symmetric in pore size through out its depth such as DURAPORE® PVDF membranes available from Millipore Corporation of Billerica Mass., or it may be asymmetric in pore size through its thickness as with MILLIPORE EXPRESS® and MILLIPORE EXPRESS® PLUS or SH_PES membranes available from Millipore Corporation of Billerica Mass. It may contain a prefilter layer if desired, either as a separate upstream layer or as an integral upstream portion of the membrane itself.

The pore size of the membrane can vary depending upon the polymer and mixture selected. Generally, it has an average pore size of from about 0.05 micron to 5 microns, preferably from about 0.05 micron to about 1 micron, more preferably from about 0.05 to about 0.65 micron.

The membrane filter may run in a deadend or normal flow (NF) format or a tangential flow (TFF) format. The choice is dependent on a number of factors, primarily the user's preference or installed filtration equipment as either works with the present invention.

Depth filters such as the MILLISTAK+® depth filters, in either lenticular or POD format, or POLYGARD® wound filters available from Millipore Corporation of Billerica Mass. allows one to trap a large volume of precipitated polymer due to its asymmetric structure and large holding capacity. This can be useful when the polymer is designed to remove impurities and to leave the target or desired biomolecule in the liquid of the remaining mixture.

Figure 1:
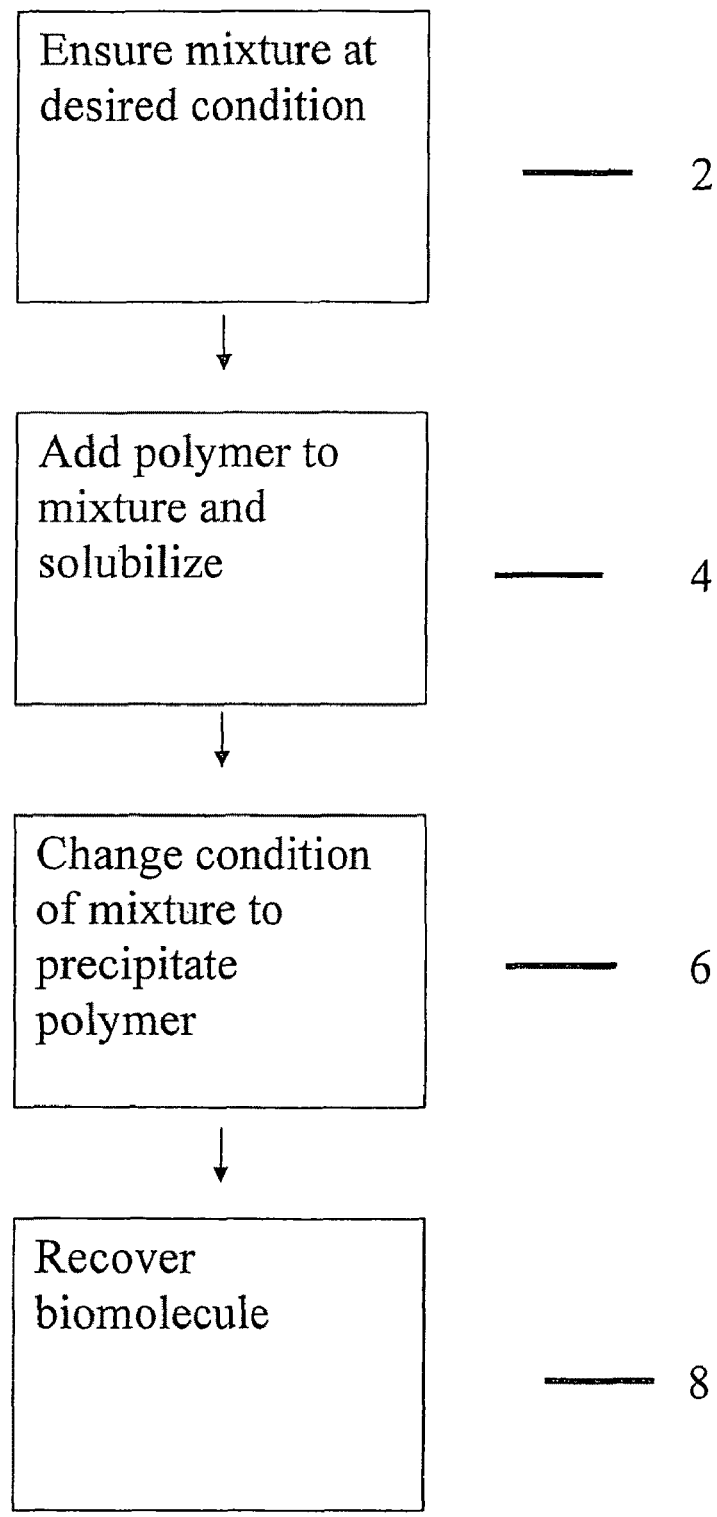
FIG. 1 shows a block diagram of a first process according to the present invention.

FIG. 1 shows a block diagram of a first process of the present invention. In the first step 2, the mixture is either conditioned to the correct parameter(s) to maintain the polymer of choice in solution or if the conditions of the mixture are already such that the polymer(s) become soluble in the mixture, no further conditioning may be required. Also, the polymer(s) may be added as a solid to an unconditioned mixture and then the mixture (containing the solid polymer(s)) may be conditioned to the correct parameters to dissolve the polymer(s) in the mixture. In the second step 4, the polymer(s) is then added to the mixture and mixed to cause it to go into solution and to make intimate contact with all the constituents of the mixture. This may occur in the bioreactor especially if the reactor is a disposable item or in a separate holding tank if desired. In the third step 6, the mixture conditions are changed to cause the polymer(s) to precipitate out of solution while retaining one or more entities of the mixture with it. The mixture and the precipitated polymer(s) are then separated from each other in the fourth step 8. As discussed above the precipitate and remaining mixture may be separated by centrifugation or filtration.

Figure 2:
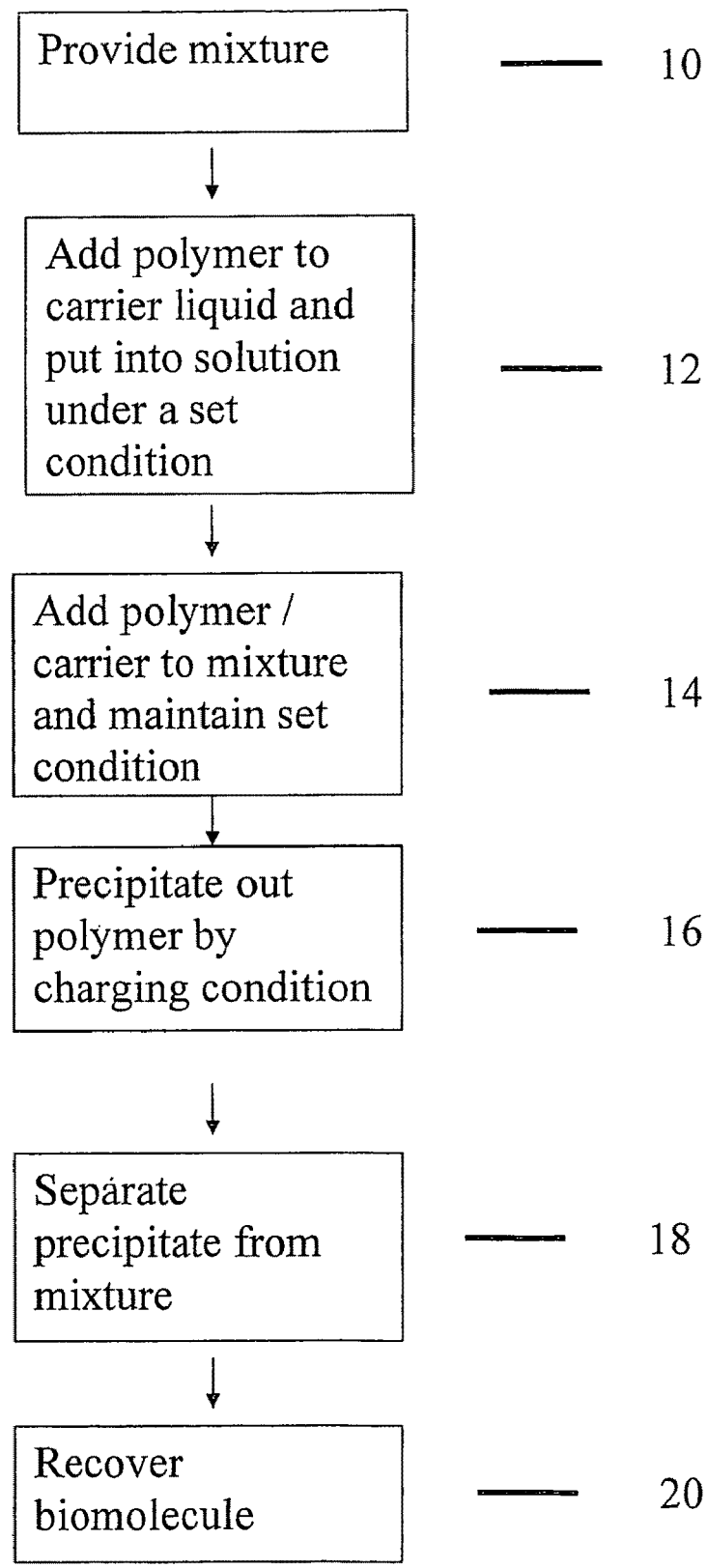
FIG. 2 shows a block diagram of a second process according to the present invention.

FIG. 2 shows a block diagram of a second process of the present invention. In the first step 10, the mixture is either conditioned to the correct parameter(s) to maintain the polymer of choice in solution before, during or after the introduction of the polymer or it is already at the desired condition. In the second step 12 which may occur separately before, simultaneously or after the first step 10, the polymer is added to a carrier liquid under conditions that allow it to go into solution. In the third step 14, the polymer in its carrier is then added to the mixture and mixed to make intimate contact with all the constituents of the mixture. In the fourth step 16, the mixture conditions are changed to cause the polymer to precipitate out of solution carrying one or more entities of the mixture with it. The mixture and the precipitated polymer are then separated from each other in the fifth step 18. As discussed above the precipitate and remaining mixture may be separated by centrifugation or filtration in a sixth step 20 and the target or desired biomolecule is recovered.

Figure 3:
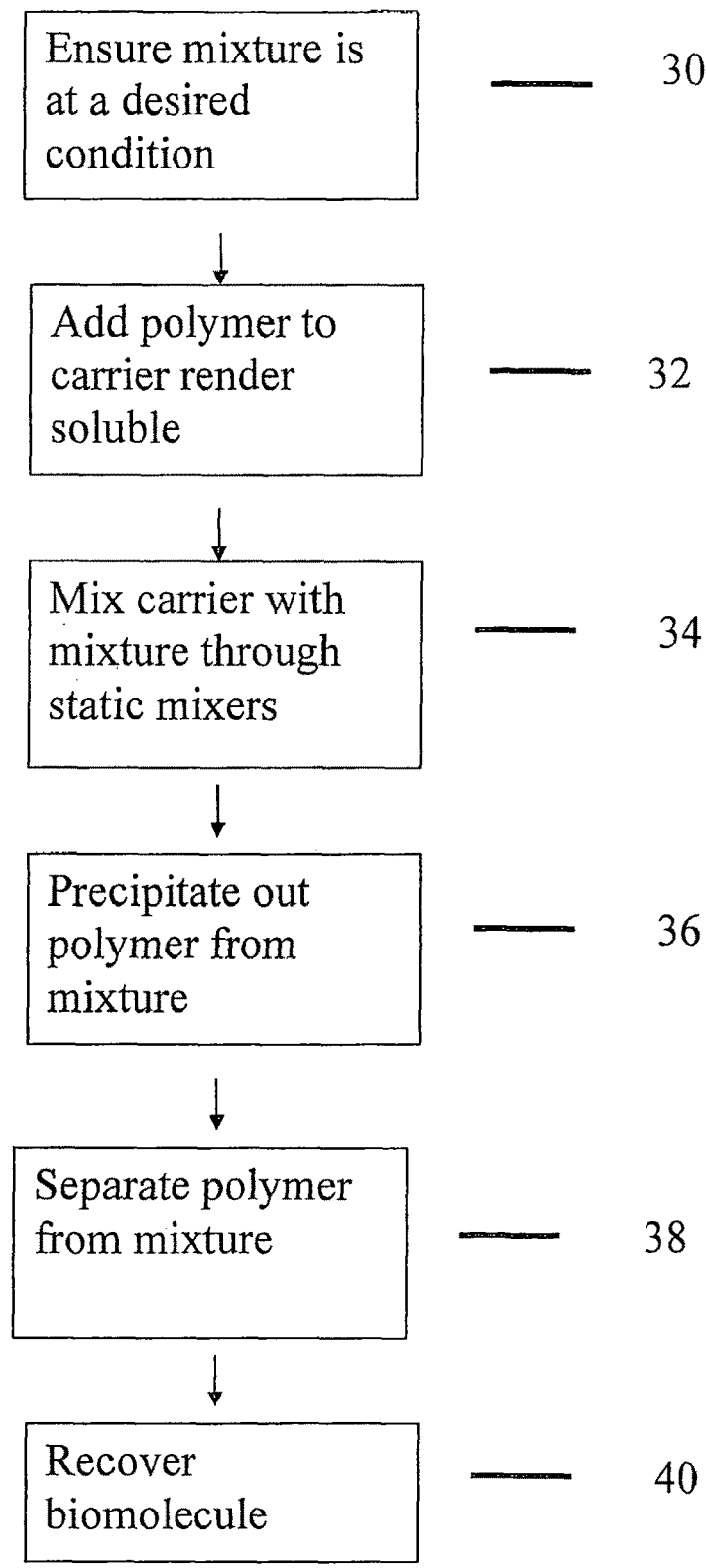
FIG. 3 shows a block diagram of a third process according to the present invention.

FIG. 3 shows a block diagram of a third process of the present invention. In the first step 30, the mixture is either conditioned to the correct parameter(s) to maintain the polymer of choice in solution before, during or after introduction of the polymer or it is already at the desired condition. In the second step 32 which may occur separately before, simultaneously or after the first step 30, the polymer is added to a carrier liquid under conditions that allow it to go into solution. In the third step 34, the polymer in its carrier is then added to the mixture through one or more static mixers to make intimate contact with all the constituents of the mixture. In the fourth step 36, the mixture conditions are changed to cause the polymer to precipitate out of solution. The mixture and the precipitated polymer are then separated from each other in the fifth step 38. As discussed above the precipitate and remaining mixture may be separated by centrifugation or filtration in a sixth step 40 and the target or desired biomolecule is recovered.

Figure 4:
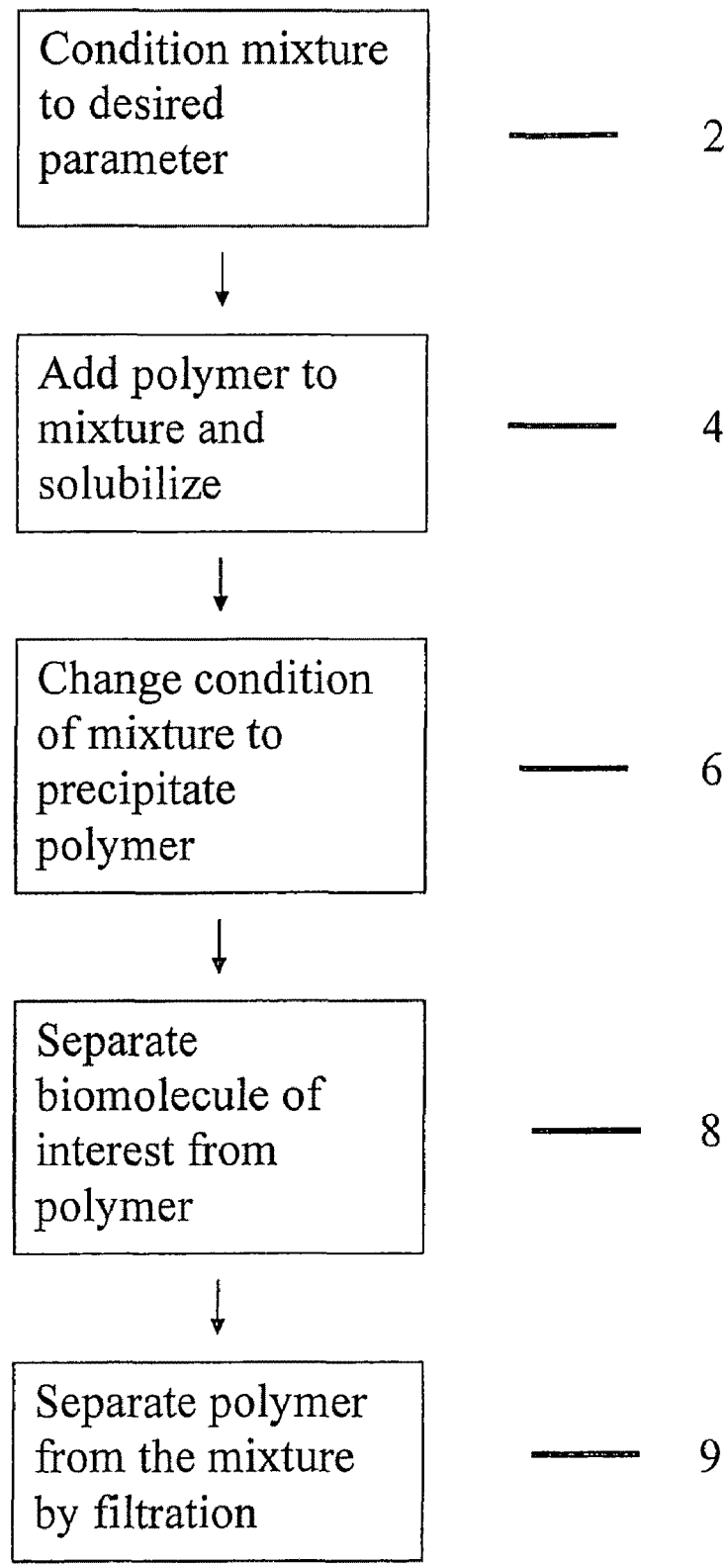
FIG. 4 shows a block diagram of a fourth process according to the present invention.

FIG. 4 shows a block diagram of the first process of the present invention as shown in FIG. 1 with an additional step. In the first step 2, the mixture is conditioned to the correct parameter(s), or if the conditions of the mixture are already such that the polymer becomes soluble in the mixture, no further conditioning may be required to maintain the polymer of choice in solution. Also, the polymer may be added as a solid to an unconditioned mixture and then the mixture (containing the solid polymer) may be conditioned to the correct parameters to dissolve the polymer in the mixture and maintain the polymer of choice in solution. In the second step 4, the polymer is then added to the mixture and mixed to cause it to go into solution and to make intimate contact with all the constituents of the mixture. In the third step 6, the mixture conditions are changed to cause the polymer to precipitate out of solution. The mixture and the precipitated polymer are then separated from each other in the fourth step 8. In the fifth step 9, the precipitate is separated from the remaining mixture by filtration. The filtration maybe by either normal flow or tangential flow filtration with any of the membranes or depth filters described above.

Figure 5:
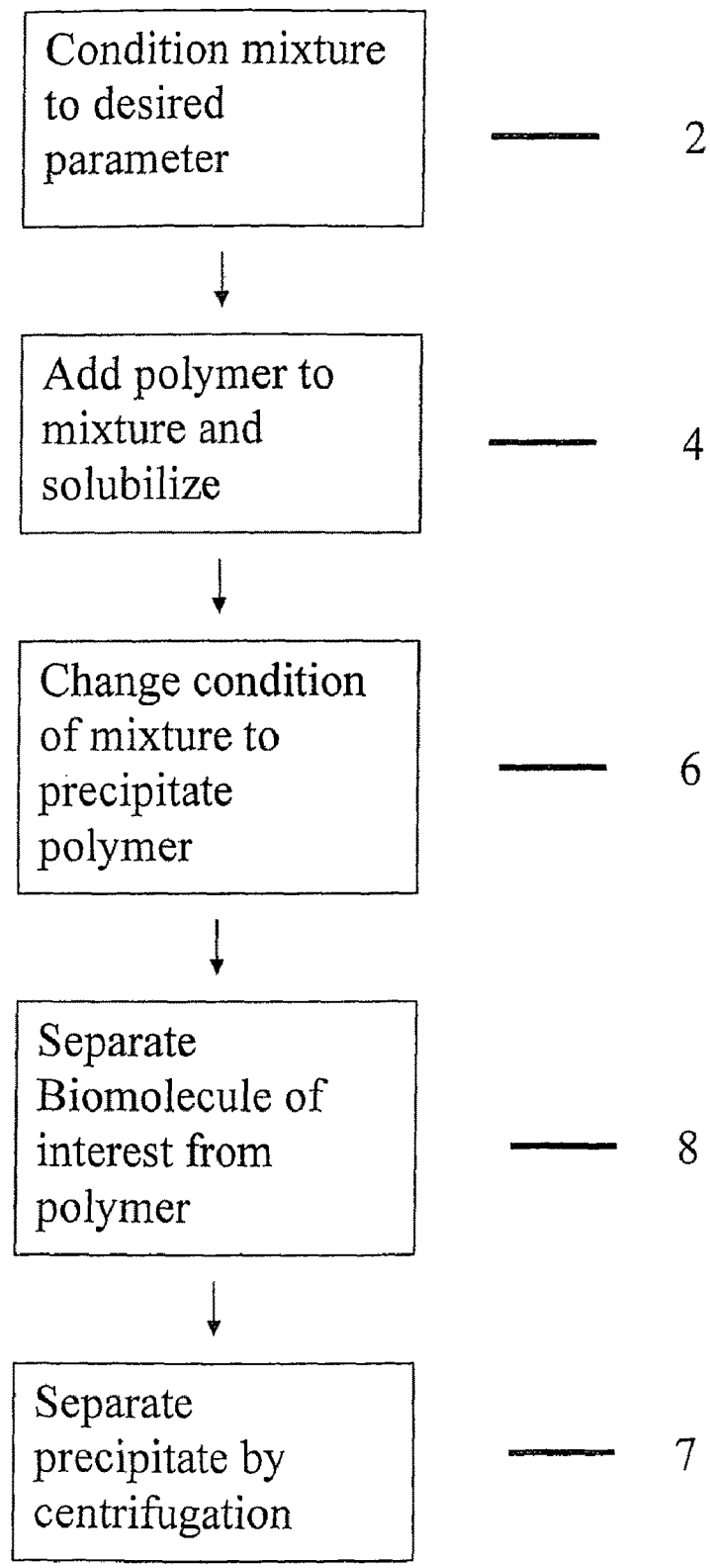
FIG. 5 shows a block diagram of a fifth process according to the present invention.

FIG. 5 shows a block diagram of the first process of the present invention as shown in FIG. 1 with an additional step. In the first step 2, the mixture is conditioned to the correct parameter(s) or if the conditions of the mixture are already such that the polymer becomes soluble in the mixture, no further conditioning may be required to maintain the polymer of choice in solution. Also, the polymer may be added as a solid to an unconditioned mixture and then the mixture (containing the solid polymer) may be conditioned to the correct parameters to dissolve the polymer in the mixture to maintain the polymer of choice in solution. In the second step 4, the polymer is then added to the mixture and mixed to cause it to go into solution and to make intimate contact with all the constituents of the mixture. In the third step 6, the mixture conditions are changed to cause the polymer to precipitate out of solution. The mixture and the precipitated polymer are then separated from each other in the fourth step 8. In the fifth step 7, the precipitate is separated from the remaining mixture by centrifugation.

The change in stimuli may be gradual or it may be done substantially instantaneous. For example, a change in pH can be done by slowly adding a pH changing material to the liquid to change the pH slowly over a span of several minutes or even hours. Alternatively, for example, a suitable amount of pH changing material can be added to the liquid at one time to cause the change in pH to occur more rapidly. More control has been found in general with incremental changes rather than immediate changes for most processes.

Examples of cationinc polyelectrolytes that exhibit this selective solubility behavior include chitosan, polyvinylpyridines (PVPs) and copolymers of PVPs such as poly(2 vinylpyridine) (P2VP) or poly(4 vinylpyridine) (P4VP), polyvinylpyridine-co-styrene (PVP-S), polyvinylpyridine-co-butyl methacrylate (PVP-BMA) as well as other primary, secondary and tertiary amine-containing polymers. These polymers are soluble at a pH lower than about 6-7 and are insoluble at a pH greater than about 5-7. When in solution, these polymers will precipitate if the pH is raised above this critical range (pH=5~7). In the context of protein purification, a solution of said cationic polyelectrolyte can be added to a fluid containing a biomolecule of interest, such as a protein in the presence of other impurities. This fluid can be for example a cell culture fluid. The polymer is added to the fluid either as a solution in a carrier liquid at a pH of about 4.5 or as a solid particulate in which the fluid is either modified to a pH of about 4.5 either before, during or after the introduction of the polymer to it (as further described below) so that the polymer binds all the negatively charged impurities, such as cells, cell fragments, nucleic acids, viruses, host cell proteins, pyrogens and endotoxins. The biomolecule of interest does not interact with the polymer given its positive net charge due to its basic pI. The pH is then raised to 5-7 or more if desired and the polymer precipitates out of solution, carrying with it all the impurities as well as any excess polymer. The precipitate can then be easily removed by centrifugation or filtration, resulting in a "purified" biomolecule containing solution.

An example of anionic polyelectrolytes that exhibit this solubility behavior is a class of copolymers of acrylic acid and methyl methacrylate or methacrylic acid and methyl methacrylate. These polymers are soluble at a pH greater than about 4-7 and insoluble at a pH lower than about 4-7. These polymers can also be used to purify proteins from complex mixtures in a bind and elute mode. For instance, a solution of these polymers can be added to a fluid containing a protein of interest in the presence of other impurities wherein the pH of the fluid is at or above about 4-7. Under these conditions, the negatively charged polymer binds the positively charged protein of interest (basic pI) while it repels the negatively charged impurities. The pH of the fluid is then lowered below about 4-7 to effect precipitation of the polymer-protein complex and any excess polymer. The precipitate can then be washed to remove any soluble or loosely bound impurities while the pH is kept below about 4-7. The protein can be subsequently eluted from the polymer with an elution buffer at high salt concentrations and a pH below about 4-7 to recover the purified protein.

Examples of a temperature sensitive polymer is agarose, which is often used in chromatography, hydroxyalkylcelluloses such as hydroxypropylcellulose; polymers and copolymers containing N-isopropylacrylamide monomer, polyethylene oxide, etc. The temperature can then be reduced or raised to cause the polymer to gel and/or precipitate out of solution.

In some cases, such as with agarose, these polymers are generally insoluble at room temperature and are soluble in water or other solvents at temperatures generally between about 80 to 120° C. They can be simply heated to cause them to dissolve, added to the mixture and then cooled to cause them to precipitate. In other cases, such as with polymers and copolymers containing N-isopropylacrylamide monomer, the polymer is soluble at a temperature below about 30 to 35° C. and will precipitate out of solution when the temperature is raised above this range.

In the case of agarose the use of gel-inhibiting agents such as various salts can depress the solubility temperature to lower temperatures, often to room temperature if desired.

Salts that can be used include lithium chloride and zinc chloride. Bases, such as sodium hydroxide or lithium hydroxide can also be used to depress the gelling temperature or to eliminate it altogether. Although the melting point for agarose is about 92 degrees, the gelling temperature is about 43 degrees. This gelling temperature can be manipulated by the modification of the agarose molecule as described above or by the addition of the above salts or by a combination thereof. For example, a cationic ligand can be attached to agarose in an amount such that the gelling temperature of the modified polymer is about 20° C. degrees with or without the addition of the above salts. The modified agarose is added, in solution at a temperature about 25° C. degrees, to the mixture (also at a temperature of about 25° C. degrees) to bind the constituents and then the temperature of the mixture is lowered to below 20° C. degrees thereby gelling the modified agarose with the constituents.

With some polymers, such as polyvinylpyridine, polyvinylpyridene-co-styrene and the like, there may be residual monomer left in the polymer as supplied. It is desirable to remove any free monomer before using the polymer. One such method is to place the polymer as purchased in an oven, preferably with an inert or low oxygen gas atmosphere such as by purging the oven several times during the process with argon or nitrogen, and maintain it at an elevated temperature (generally between 100 and 200° C., preferably about 120° C.) and under a vacuum so as to drive off all monomer present (generally about 24 hours).

Additionally, with some polymers, such as polyvinylpyridine, polyvinylpyridene-co-sytrene and the like, it is desirable to select higher molecular weight polymers (200,000 molecular weight or higher) as they have been found to more freely precipitate out of solution than lower molecular weight polymers. This means that one can be sure that no residual polymer is left in the solution after precipitation.

In some instances, precipitation by itself may be slow or incomplete. In those instances, one can repeat the process of changing the stimuli conditions two or more times, add precipitant enhancers such as glass beads, salts and the like, vary the temperature of the process and the like to enhance the precipitation.

Typical polymer concentrations in the carrier solvent are between 1-20% by weight depending on the viscosity of the solution. It is preferred that the concentration be as high as possible to minimize dilution of the feedstock. Practically, polymer solutions in the 10-20% are preferred to achieve a good balance between viscosity and dilution of the feedstock. The final concentration of the polymer in the feedstock may depend on the amount of impurities in the feedstock but it is typically between 0.01% to 2% by weight and more specifically between 0.05% and 0.1%.

In some processes one may use two or more polymers either simultaneously or sequentially to enhance the impurity removal. For example, one may use chitosan as the first polymer and conduct a first purification step. This fluid is separated from the precipitated chitosan/impurities and then treated with a second polymer such as a polyvinylpyridine to further remove impurities.

The recovered biomolecule may then undergo one or more additional processing steps depending on whether it is contained within the liquid of the mixture or is bound to the precipitated polymer.

A method of sequential precipitation may be used to recover the biomolecule of interest. In such a method, a first precipitation as described above would be used to remove impurities and the precipitated polymer/impurities mass would be separated from the target biomolecule containing solution. The solution would then be mixed with a stimuli responsive polymer containing a ligand capable of binding to the biomolecule of interest at a solution condition at which the polymer is soluble. Following methods described previously, the solution conditions would be changed so as to precipitate the polymer and bound biomolecule. The polymer/biomolecule would then be separated as previously described, the biomolecule eluted or otherwise separated from the polymer, and the recovered biomolecule further processed as needed.

As the biomolecule of interest is in the liquid, it may, if needed or desired undergo one or more known process steps including but not limited to chromatography steps such as ion exchange, hydrophobic interaction or affinity chromatography, various filtration steps such as high performance tangential flow filtration (HPTFF), viral removal/inactivation steps, final filtration and the like. Alternatively, the biomolecule of interest present in the liquid may be used as is without the need for further purification steps.

The chromatography may be column based using solid bead media or monoliths or through a membrane absorber or chromatography device. The step if desired can be a classic bind/elute or a flow through mode of chromatography.

Also the biomolecule of interest may undergo further purification without the need for chromatography steps such as through the use of high performance tangential flow filtration using one or more charged membranes.

Additionally, in several embodiments, no further purification is required. One may if desired add additional steps to ensure that viruses have been removed or inactivated or to be sure no residual precipitate remains.

A further variation uses an affinity step to bind and then elute the desired biomolecule. Affinity ligands such as Protein A either on a solid matrix such as a bead or membrane may be used.

In one embodiment of the present invention, the current process simply replaces a clarification step and prefilter step in a normal biological product process train.

In another embodiment, it replaces clarification, prefiltration and at least one chromatography step by directly purifying the biomolecule of interest from the starting materials.

In an additional embodiment, it replaces a cell harvest or biomolecule collection step by being added directly to the bioreactor or fermentor. This also eliminates the need for clarification, prefiltration and potentially at least one chromatography step by directly purifying the biomolecule of interest from the starting materials.

In any of the embodiments of the present invention the protein thus recovered may be formulated in a pharmaceutically acceptable carrier and is used for various diagnostic, therapeutic or other uses known for such molecules.

The mixture that is the starting material of the process will vary depending upon the cell line in which it was grown as well as the conditions under which it is grown and harvested. For example, in most CHO cell processes the cells express the molecule outside of the cell wall into the media. One tries not to rupture the cells during harvest in order to reduce the amount impurities in the mixture. However, some cells during grow and harvesting may rupture due to shear or other handling conditions or die and lyse, spilling their contents into the mixture. In bacteria cell systems, the biomolecule is often kept with the cellular wall or it may actually be part of the cellular wall (Protein A). In these systems the cell walls need to be disrupted or lysed in order to recover the biomolecule of interest.

The target molecule to be purified can be any biomolecule, preferably a protein, in particular, recombinant protein produced in any host cell, including but not limited to, Chinese hamster ovary (CHO) cells, Per.C6® cell lines available from Crucell of the Netherlands, myeloma cells such as NS0 cells, other animal cells such as mouse cells, insect cells, or microbial cells such as E. coli or yeast. Additionally, the mixture may be a fluid derived from an animal modified to produce a transgenic fluid such as milk or blood that contains the biomolecule of interest. Optimal target proteins are antibodies, immunoadhesins and other antibody-like molecules, such as fusion proteins including a $C_H2/C_H3$ region. In particular, this product and process can be used for purification of recombinant humanized monoclonal antibodies such as (RhuMAb) from a conditioned harvested cell culture fluid (HCCF) grown in Chinese hamster ovary (CHO) cells expressing RhuMAb.

Antibodies within the scope of the present invention include, but are not limited to: anti-HER2 antibodies including Trastuzumab (HERCEPTIN®) (Carter et al., *Proc. Natl. Acad. Sci. USA*, 89:4285-4289 (1992), U.S. Pat. No. 5,725, 856); anti-CD20 antibodies such as chimeric anti-CD20 "C2B8" as in U.S. Pat. No. 5,736,137 (RITUXAN.®), a chimeric or humanized variant of the 2H7 antibody as in U.S. Pat. No. 5,721,108, B1, or Tositumomab (BEXXAR.®); anti-IL-8 (St John et al., *Chest*, 103:932 (1993), and International Publication No. WO 95/23865); anti-VEGF antibodies including humanized and/or affinity matured anti-VEGF antibodies such as the humanized anti-VEGF antibody huA4.6.1 AVASTIN®. (Kim et al., *Growth Factors*, 7:53-64 (1992), International Publication No. WO 96/30046, and WO 98/45331, published Oct. 15, 1998); anti-PSCA antibodies (WO01/40309); anti-CD40 antibodies, including S2C6 and humanized variants thereof (WO00/75348); anti-CD11a (U.S. Pat. No. 5,622,700, WO 98/23761, Steppe et al., *Transplant Intl*. 4:3-7 (1991), and Hourmant et al., *Transplantation* 58:377-380 (1994)); anti-IgE (Presta et al., *J. Immunol*. 151: 2623-2632 (1993), and International Publication No. WO 95/19181); anti-CD18 (U.S. Pat. No. 5,622,700, issued Apr. 22, 1997, or as in WO 97/26912, published Jul. 31, 1997); anti-IgE (including E25, E26 and E27; U.S. Pat. No. 5,714, 338, issued Feb. 3, 1998 or U.S. Pat. No. 5,091,313, issued Feb. 25, 1992, WO 93/04173 published Mar. 4, 1993, or International Application No. PCT/US98/13410 filed Jun. 30, 1998, U.S. Pat. No. 5,714,338); anti-Apo-2 receptor antibody (WO 98/51793 published Nov. 19, 1998); anti-TNF-α antibodies including cA2 (REMICADE®), CDP571 and MAK-195 (See, U.S. Pat. No. 5,672,347 issued Sep. 30, 1997, Lorenz et al. *J. Immunol*. 156(4):1646-1653 (1996), and Dhainaut et al. *Crit. Care Med*. 23(9):1461-1469 (1995)); anti-Tissue Factor (TF) (European Patent No. 0 420 937 B1 granted Nov. 9, 1994); anti-human $α_4β_7$ integrin (WO 98/06248 published Feb. 19, 1998); anti-EGFR (chimerized or humanized 225 antibody as in WO 96/40210 published Dec. 19, 1996); anti-CD3 antibodies such as OKT3 (U.S. Pat. No. 4,515,893 issued May 7, 1985); anti-CD25 or anti-tac antibodies such as CHI-621 (SIMULECT®) and (ZENAPAX®) (See U.S. Pat. No. 5,693,762 issued Dec. 2, 1997); anti-CD4 antibodies such as the cM-7412 antibody (Choy et al. *Arthritis Rheum* 39(1):52-56 (1996)); anti-CD52 antibodies such as CAMPATH-1H (Riechmann et al. *Nature* 332: 323-337 (1988)); anti-Fc receptor antibodies such as the M22 antibody directed against FcγRI as in Graziano et al. *J. Immunol*. 155(10):4996-5002 (1995); anti-carcinoembryonic antigen (CEA) antibodies such as hMN-14 (Sharkey et al. *Cancer Res*. 55(23 Suppl): 5935s-5945s (1995); antibodies directed against breast epithelial cells including huBrE-3, hu-Mc 3 and CHL6 (Ceriani et al. *Cancer Res*. 55(23): 5852s-5856s (1995); and Richman et al. *Cancer Res*. 55(23 Supp): 5916s-5920s (1995)); antibodies that bind to colon carcinoma cells such as C242 (Litton et al. *Eur J. Immunol*. 26(1): 1-9 (1996)); anti-CD38 antibodies, e.g. AT 13/5 (Ellis et al. *J Immunol*. 155(2):925-937 (1995)); anti-CD33 antibodies such as Hu M195 (Jurcic et al. *Cancer Res* 55(23 Suppl):5908s-5910s (1995) and CMA-676 or CDP771; anti-CD22 antibodies such as LL2 or LymphoCide (Juweid et al. *Cancer Res* 55(23 Suppl):5899s-5907s (1995)); anti-EpCAM antibodies such as 17-1A (PANOREX®); anti-GpIIb/IIIa antibodies such as abciximab or c7E3 Fab (REOPRO®); anti-RSV antibodies such as MEDI-493 (SYNAGIS®); anti-CMV antibodies such as PROTOVIR®; anti-HIV antibodies such as PRO542; anti-hepatitis antibodies such as the anti-Hep B antibody OSTAVIR®; anti-CA 125 antibody OvaRex; anti-idiotypic GD3 epitope antibody BEC2; anti-αvβ3 antibody VITAXIN®; anti-human renal cell carcinoma antibody such as ch-G250; ING-1; anti-human 17-1A antibody (3622W94); anti-human colorectal tumor antibody (A33); anti-human melanoma antibody R24 directed against GD3 ganglioside; anti-human squamous-cell carcinoma (SF-25); and anti-human leukocyte antigen (HLA) antibodies such as Smart ID10 and the anti-HLA DR antibody Oncolym (Lym-1). The preferred target antigens for the antibody herein are: HER2 receptor, VEGF, IgE, CD20, CD11a, and CD40.

Aside from the antibodies specifically identified above, the skilled practitioner could generate antibodies directed against an antigen of interest, e.g., using the techniques described below.

The antibody herein is directed against an antigen of interest. Preferably, the antigen is a biologically important polypeptide and administration of the antibody to a mammal suffering from a disease or disorder can result in a therapeutic benefit in that mammal. However, antibodies directed against non-polypeptide antigens (such as tumor-associated glycolipid antigens; see U.S. Pat. No. 5,091,178) are also contemplated. Where the antigen is a polypeptide, it may be a transmembrane molecule (e.g. receptor) or ligand such as a growth factor. Exemplary antigens include those proteins described in section (3) below. Exemplary molecular targets for antibodies encompassed by the present invention include CD proteins such as CD3, CD4, CD8, CD19, CD20, CD22, CD34, CD40; members of the ErbB receptor family such as the EGF receptor, HER2, HER3 or HER4 receptor; cell adhesion molecules such as LFA-1, Mac1, p150,95, VLA-4, ICAM-1, VCAM and $\alpha v/\beta 3$ integrin including either $\alpha$ or $\beta$ subunits thereof (e.g. anti-CD11a, anti-CD18 or anti-CD11b antibodies); growth factors such as VEGF; IgE; blood group antigens; flk2/flt3 receptor; obesity (OB) receptor; mpl receptor; CTLA-4; protein C, or any of the other antigens mentioned herein. Antigens to which the antibodies listed above bind are specifically included within the scope herein.

Soluble antigens or fragments thereof, optionally conjugated to other molecules, can be used as immunogens for generating antibodies. For transmembrane molecules, such as receptors, fragments of these (e.g. the extracellular domain of a receptor) can be used as the immunogen. Alternatively, cells expressing the transmembrane molecule can be used as the immunogen. Such cells can be derived from a natural source (e.g. cancer cell lines) or may be cells which have been transformed by recombinant techniques to express the transmembrane molecule.

Other antigens and forms thereof useful for preparing antibodies will be apparent to those in the art.

Polyclonal antibodies can also be purified in the present invention. Polyclonal antibodies are preferably raised in animals by multiple subcutaneous (sc) or intraperitoneal (ip) injections of the relevant antigen and an adjuvant. It may be useful to conjugate the antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C$ NR, where R and $R^1$ are different alkyl groups.

Animals are immunized against the antigen, immunogenic conjugates, or derivatives by combining, e.g., 100 µg or 5 µg of the protein or conjugate (for rabbits or mice, respectively) with 3 volumes of Freund's complete adjuvant and injecting the solution intradermally at multiple sites. One month later the animals are boosted with ⅕ to ⅒ the original amount of antigen or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal antibodies are of interest in the present invention and may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster or macaque monkey, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, Pro-Sep® Protein A media available from Millipore Corporation of Billerica, Mass., hydroxyapatite chromatography, gel electrophoresis, dialysis, or affinity chromatography. Preferably the Protein A chromatography procedure described herein is used.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells.

The DNA also may be modified, for example, by substituting the coding sequence for human heavy- and light-chain constant domains in place of the homologous murine sequences (U.S. Pat. No. 4,816,567; Morrison, et al., *Proc. Natl. Acad. Sci. USA*, 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

In a further embodiment, monoclonal antibodies can be isolated from antibody phage libraries generated using the techniques described in McCafferty et al., *Nature*, 348:552-554 (1990). Clackson et al., *Nature*, 352:624-628 (1991) and Marks et al., *J. Mol. Biol.*, 222:581-597 (1991) describe the isolation of murine and human antibodies, respectively, using phage libraries. Subsequent publications describe the production of high affinity (nM range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nuc. Acids. Res.*, 21:2265-2266 (1993)). Thus, these techniques are viable alternatives to traditional hybridoma techniques for isolation of monoclonal antibodies.

A humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321:522-525 (1986); Riechmann et al., *Nature*, 332:323-327 (1988); Verhoeyen et al., *Science*, 239: 1534-1536 (1988)), by substituting rodent CDRs or CDR sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human FR for the humanized antibody (Sims et al., *J. Immunol.*, 151:2296 (1993)). Another method uses a particular framework derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immunol.*, 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA*, 90:2551 (1993); Jakobovits et al., *Nature*, 362:255-258 (1993); Bruggermann et al., *Year in Immuno.*, 7:33 (1993); and Duchosal et al. *Nature* 355:258 (1992). Human antibodies can also be derived from phage-display libraries (Hoogenboom et al., *J. Mol. Biol.*, 227:381 (1991); Marks et al., *J. Mol. Biol.*, 222:581-597 (1991); Vaughan et al. *Nature Biotech* 14:309 (1996)).

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992) and Brennan et al., *Science*, 229: 81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form $F(ab')_2$ fragments (Carter et al., Bio/Technology 10: 163-167 (1992)). According to another approach, $F(ab')_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185.

Multispecific antibodies have binding specificities for at least two different antigens. While such molecules normally will only bind two antigens (i.e. bispecific antibodies, BsAbs), antibodies with additional specificities such as trispecific antibodies are encompassed by this expression when used herein.

Methods for making bispecific antibodies are known in the art. Traditional production of full length bispecific antibodies is based on the coexpression of two immunoglobulin heavy chain-light chain pairs, where the two chains have different specificities (Millstein et al., *Nature*, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.*, 10:3655-3659 (1991).

According to another approach described in WO96/27011, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994). Alternatively, the antibodies can be "linear antibodies" as described in Zapata et al. *Protein Eng.* 8(10):1057-1062 (1995). Briefly, these antibodies comprise a pair of tandem Fd segments ($V_H$-$C_H$1-$V_H$-$C_H$1) which form a pair of antigen binding regions. Linear antibodies can be bispecific or monospecific.

Antibodies with more than two valencies are contemplated. For example, trispecific antibodies can be prepared. Tutt et al. *J. Immunol.* 147: 60 (1991).

The simplest and most straightforward immunoadhesin design combines the binding domain(s) of the adhesin (e.g. the extracellular domain (ECD) of a receptor) with the hinge and Fc regions of an immunoglobulin heavy chain. Ordinarily, when preparing the immunoadhesins of the present invention, nucleic acid encoding the binding domain of the adhesin will be fused C-terminally to nucleic acid encoding the N-terminus of an immunoglobulin constant domain sequence, however N-terminal fusions are also possible.

Typically, in such fusions the encoded chimeric polypeptide will retain at least functionally active hinge, $C_H2$ and $C_H3$ domains of the constant region of an immunoglobulin heavy chain. Fusions are also made to the C-terminus of the Fc portion of a constant domain, or immediately N-terminal to the $C_H1$ of the heavy chain or the corresponding region of the light chain. The precise site at which the fusion is made is not critical; particular sites are well known and may be selected in order to optimize the biological activity, secretion, or binding characteristics of the immunoadhesin.

In a preferred embodiment, the adhesin sequence is fused to the N-terminus of the Fc domain of immunoglobulin $G_1$ ($IgG_1$). It is possible to fuse the entire heavy chain constant region to the adhesin sequence. However, more preferably, a sequence beginning in the hinge region just upstream of the papain cleavage site which defines IgG Fc chemically (i.e. residue 216, taking the first residue of heavy chain constant region to be 114), or analogous sites of other immunoglobulins is used in the fusion. In a particularly preferred embodiment, the adhesin amino acid sequence is fused to (a) the hinge region and $C_H2$ and $C_H3$ or (b) the $C_H1$, hinge, $C_H2$ and $C_H3$ domains, of an IgG heavy chain.

For bispecific immunoadhesins, the immunoadhesins are assembled as multimers, and particularly as heterodimers or heterotetramers. Generally, these assembled immunoglobulins will have known unit structures. A basic four chain structural unit is the form in which IgG, IgD, and IgE exist. A four chain unit is repeated in the higher molecular weight immunoglobulins; IgM generally exists as a pentamer of four basic units held together by disulfide bonds. IgA globulin, and occasionally IgG globulin, may also exist in multimeric form in serum. In the case of multimer, each of the four units may be the same or different.

Various exemplary assembled immunoadhesins within the scope herein are schematically diagrammed below:

(a) $AC_L$-$AC_L$;
(b) $AC_H$-($AC_H$, $AC_L$-$AC_H$, $AC_L$-$V_HC_H$, or $V_LC_L$-$AC_H$);
(c) $AC_L$-$AC_H$-($AC_L$-$AC_H$, $AC_L$-$V_HC_H$, $V_LC_L$-$AC_H$, or $V_LC_L$-$V_HC_H$)
(d) $AC_L$-$V_HC_H$-($AC_H$, or $AC_L$-$V_HC_H$, or $V_LC_L$-$AC_H$);
(e) $V_LC_L$-$AC_H$-($AC_L$-$V_HC_H$, or $V_LC_L$-$AC_H$); and
(f) (A-Y)$_n$-($V_LC_L$-$V_HC_H$)$_2$, wherein each A represents identical or different adhesin amino acid sequences;

$V_L$ is an immunoglobulin light chain variable domain;
$V_H$ is an immunoglobulin heavy chain variable domain;
$C_L$ is an immunoglobulin light chain constant domain;
$C_H$ is an immunoglobulin heavy chain constant domain;
n is an integer greater than 1;
Y designates the residue of a covalent cross-linking agent.

In the interests of brevity, the foregoing structures only show key features; they do not indicate joining (J) or other domains of the immunoglobulins, nor are disulfide bonds shown. However, where such domains are required for binding activity, they shall be constructed to be present in the ordinary locations which they occupy in the immunoglobulin molecules.

Alternatively, the adhesin sequences can be inserted between immunoglobulin heavy chain and light chain sequences, such that an immunoglobulin comprising a chimeric heavy chain is obtained. In this embodiment, the adhesin sequences are fused to the 3' end of an immunoglobulin heavy chain in each arm of an immunoglobulin, either between the hinge and the $C_H2$ domain, or between the $C_H2$ and $C_H3$ domains. Similar constructs have been reported by Hoogenboom, et al., *Mol. Immunol.* 28:1027-1037 (1991).

Although the presence of an immunoglobulin light chain is not required in the immunoadhesins of the present invention, an immunoglobulin light chain might be present either covalently associated to an adhesin-immunoglobulin heavy chain fusion polypeptide, or directly fused to the adhesin. In the former case, DNA encoding an immunoglobulin light chain is typically coexpressed with the DNA encoding the adhesin-immunoglobulin heavy chain fusion protein. Upon secretion, the hybrid heavy chain and the light chain will be covalently associated to provide an immunoglobulin-like structure comprising two disulfide-linked immunoglobulin heavy chain-light chain pairs. Methods suitable for the preparation of such structures are, for example, disclosed in U.S. Pat. No. 4,816,567, issued 28 Mar. 1989.

Immunoadhesins are most conveniently constructed by fusing the cDNA sequence encoding the adhesin portion in-frame to an immunoglobulin cDNA sequence. However, fusion to genomic immunoglobulin fragments can also be used (see, e.g. Aruffo et al., *Cell* 61:1303-1313 (1990); and Stamenkovic et al., *Cell* 66:1133-1144 (1991)). The latter type of fusion requires the presence of Ig regulatory sequences for expression. cDNAs encoding IgG heavy-chain constant regions can be isolated based on published sequences from cDNA libraries derived from spleen or peripheral blood lymphocytes, by hybridization or by polymerase chain reaction (PCR) techniques. The cDNAs encoding the "adhesin" and the immunoglobulin parts of the immunoadhesin are inserted in tandem into a plasmid vector that directs efficient expression in the chosen host cells.

In other embodiments, the protein to be purified is one which is fused to, or conjugated with, a $C_H2$/$C_H3$ region. Such fusion proteins may be produced so as to increase the serum half-life of the protein. Examples of biologically important proteins which can be conjugated this way include renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; Protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD3, CD4, CD8, CD19, CD20, CD34, and CD40; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; a tumor associated antigen such as HER2, HER3 or HER4 receptor; and fragments of any of the above-listed polypeptides.

EXAMPLES

The following examples are offered by way of illustration and not by way of limitation. The disclosures of all citations in the specification are expressly incorporated herein by reference.

Example 1

This Example illustrates the removal of residual 4-vinyl pyridine monomer from poly(4-vinylpyridine).

Linear poly(4-vinylpyridine), (P4VP) MW 200,000 obtained form Scientific Polymer Products, Inc., was spread evenly on a glass dish and placed in a vacuum oven. The atmosphere inside the oven was purged with argon for 5 minutes several times to remove oxygen. The pressure in the oven was reduced to 0.1 in mercury using a mechanical vacuum pump and subsequently the temperature was raised to 120° C. The polymer was subjected to these conditions for a total of 24 hours. During this time, the atmosphere inside the oven was purged with argon for 5 minutes several times. At the end of the heating period, the oven temperature was lowered to room temperature and the oven was purged with argon several times before opening the door. The resulting polymer did not have a noticeable odor, whereas the untreated polymer has a distinct odor of 4-vinyl pyridine monomer. The amount of residual 4-vinyl pyridine monomer present in the treated polymer was not detectable by gel permeation chromatography whereas the untreated polymer had 0.05% (w/w) residual 4-vinyl pyridine monomer

Example 2

This example illustrates the removal of residual 2-vinyl pyridine monomer from poly(2-vinylpyridine).

Linear poly(2-vinylpyridine), (P2VP) MW 200,000 obtained form Scientific Polymer Products, Inc., was treated exactly according to the process of example 1. The resulting polymer did not have a noticeable odor, whereas the untreated polymer has a distinct odor of 2-vinyl pyridine monomer.

Example 3

This Example illustrates the removal of residual 4-vinyl pyridine and styrene monomers from poly(4-vinylpyridine-co-styrene).

Linear poly(4-vinylpyridine-co-styrene), (P4VP-S), 10% styrene content, obtained form Scientific Polymer Products, Inc., was treated exactly according to the process of example 1. The resulting polymer did not have a noticeable odor, whereas the untreated polymer has a distinct odor of 4-vinyl pyridine and styrene monomers.

Example 4

This Example illustrates the preparation of a poly(4-vinylpyridine) (P4VP) solution.

A 20% (w/w) solution of P4VP was prepared by dissolving 20 g purified P4VP, from example 1, in 80 g 1.0 M hydrochloric acid with continuous agitation for 16 hours at room temperature. The resulting viscous solution was clear and had a slight yellow color.

Example 5

This Example illustrates the preparation of a (P2VP) solution.

A 20% (w/w) solution of P2VP was prepared by dissolving 20 g purified P2VP, from example 2, in 80 g 1.0 M hydrochloric acid with continuous agitation for 16 hours at room temperature. The resulting viscous solution was clear and had a slight yellow color.

Example 6

This Example illustrates the preparation of a P4VP-S solution.

A 10% (w/w) solution of P4VP-S was prepared by dissolving 10 g purified P4VP-S, from example 3, in 90 g 1.0 M hydrochloric acid with continuous agitation for 16 hours at room temperature. The resulting viscous solution was hazy.

Example 7

This Example illustrates the preparation of a chitosan solution.

A 2.5% (w/w) solution of chitosan was prepared by dissolving 2.5 g chitosan, high molecular weight, obtained form Sigma-Aldrich, in 97.5 g 0.5 M hydrochloric acid with continuous agitation for 16 hours at room temperature.

Example 8

This Example illustrates the preparation of a P4VP solution.

A 10% (w/w) solution of P4VP was prepared by dissolving 10 g purified P4VP, from example 1, in 90 g 1.0 M hydrochloric acid with continuous agitation for 16 hours at room temperature. The resulting viscous solution was clear.

Example 9

This Example illustrates the response of a "smart" polymer as a result of a pH stimulus.

About 5 ml of the P4VP solution from example 8 were placed in a test tube, the pH was measured to be below 5. The pH of this solution was slowly raised to 7 by a dropwise addition of 2N NaOH. The polymer precipitated out of solution, the color of the precipitate was white and the decanted liquid was completely clear and colorless suggesting the absence of any polymer.

Example 10

This Example illustrates the removal of a negatively charged dye from solution.

About 3 ml of the P4VP solution from example 8 were added to about 5 ml of a solution containing 0.1 ml Ponceau-S (negatively charged dye, red in color) in water. After the addition, the solution was clear and red in color. The pH of the solution was slowly raised to 7 with a few drops of 2N NaOH, a red precipitate was formed and a clear and colorless liquid was recovered by decanting. The red precipitate contains all the Ponceau S dye that was effectively removed from the liquid phase.

Example 11

This Example illustrates the removal of negatively charged impurities from a cell culture medium containing a monoclonal antibody The starting feed for the experiment is this example was a raw cell culture medium from a non-expressing line of Chinese Hamster Ovary (CHO) cells incubated in a Wave bioreactor for ten days (sample C), the appearance of this liquid was turbid (due to suspended cell mass) and slightly yellow. Sample C was spiked with a monoclonal antibody (MAb) to a final concentration of about 1 g/L MAb (sample CP), the appearance of this liquid did not change following the spike.

The pH of sample C was adjusted to 4.8 with the addition of HCl. To this liquid, the P4VP solution of example 8 was added in an amount equivalent to about 20% of the starting volume of pH adjusted sample, the appearance of this sample did not change. The pH of the liquid was then slowly raised to 7 by the dropwise addition of 2N NaOH while mixing. A pale yellow precipitate was formed, which was easily removed by decanting, the resulting liquid was completely clear and colorless (sample T). This procedure was repeated with sample CP to yield a completely clear and colorless liquid (sample TP) after the removal of the yellow precipitate.

All samples were filtered through 0.2 μm PVDF membranes and analyzed for the presence of host cell proteins (CHO cell proteins), MAb and DNA. FIGS. 6A and B show SDS-PAGE data for sample C indicates the presence of a multitude of proteins of varying molecular weights due to CHO cell proteins. Sample CP contains the same population of CHO cell proteins as in sample C as well as the MAb (characteristic molecular weight). Data for sample T shows no visible bands indicating the absence of proteins. Data for sample TP shows only the characteristic bands for the MAb indicating the presence of pure MAb. Gel electrophoresis data in FIG. 7 shows the presence of DNA in samples C and CP while no DNA bands were visible in samples T and TP indicating the absence of DNA. This example shows that this technique is capable of purifying a MAb from a complex mixture of suspended material (cell mass) as well as soluble molecules (host cell proteins and DNA) to result in a pure MAb solution.

Figure 6B:
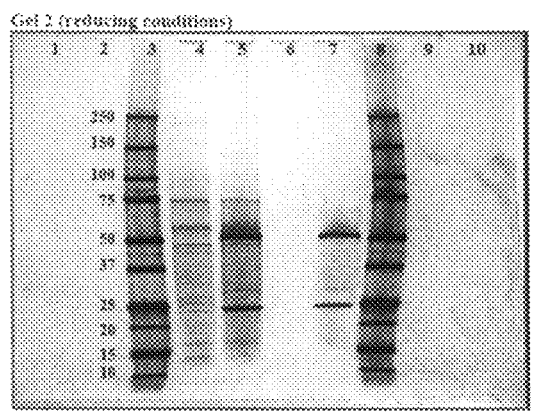

SDS-PAGE data as shown in FIGS. 6 A and B:
Lanes 3 and 8 are the molecular weight standards. Lane 4 is sample C. Lane 5 is sample CP. Lane 6 is sample T. Lane 7 is sample TP.

Gel electrophoresis data as shown in FIG. 7:
Lane 5 is the molecular weight standards. Lane 6 is sample C. Lane 7 is sample CP. Lane 8 is sample T. Lane 9 is sample TP.

Example 12

This Example illustrates the use of PVP-S for the removal of cell mass from a cell culture fluid containing a monoclonal antibody The starting feed for the experiment is this example was a raw cell culture fluid from an IgG expressing line of Chinese Hamster Ovary (CHO) cells incubated in a Wave bioreactor, the appearance of this liquid was turbid (due to suspended cell mass) and slightly yellow.

The pH of the starting feed was adjusted to 4.8 with the addition of HCl. To this fluid, the PVP-S solution of example 6 was added in an amount equivalent to about 0.1% by weight of dry PVP-S relative to the volume of the starting feed, the appearance of this sample did not change. The pH of the liquid was then quickly raised to 7 by addition of 2N NaOH while mixing vigorously. A pale yellow precipitate was formed, which was easily removed by decanting, the resulting liquid was completely clear.

Example 13

This Example illustrates the use of chitosan for the removal of cell mass from a cell culture fluid containing a monoclonal antibody The starting feed for the experiment is this example was a raw cell culture fluid from an IgG expressing line of Chinese Hamster Ovary (CHO) cells incubated in a Wave bioreactor, the appearance of this liquid was turbid (due to suspended cell mass) and slightly yellow.

The pH of the starting feed was adjusted to 6.5 with the addition of HCl. To this fluid, the chitosan solution of example 7 was added in an amount equivalent to about 0.06% by weight of dry chitosan relative to the volume of the starting feed, the appearance of this sample did not change. The pH of the liquid was then raised to 7.3 by addition of 1N NaOH while mixing. A precipitate was formed, which was easily removed by decanting, the resulting liquid was completely clear. The turbidity of the supernatant was measured to be less than 5 NTU, the turbidity of the starting feed was in excess of 300 NTU. The removal of DNA by this process was measured to be about 1.5 logs.

Example 14

This Example illustrates the use of a mixture of P4VP and chitosan for the removal of cell mass from a cell culture fluid containing a monoclonal antibody The starting feed for the experiment is this example was a raw cell culture fluid from an IgG expressing line of Chinese Hamster Ovary (CHO) cells incubated in a Wave bioreactor, the appearance of this liquid was turbid (due to suspended cell mass) and slightly yellow.

The pH of the starting feed was adjusted to 4 with the addition of HCl. To this fluid, the P4VP solution of example 8 and the chitosan solution of example 7 were added in amounts equivalent to about 0.1% and 0.06%, respectively, by weight of dry polymer relative to the volume of the starting feed, the appearance of this sample did not change. The pH of the liquid was then raised to 7.3 by addition of 1N NaOH while mixing. A first precipitate was formed at pH 5 and a second precipitate was observed at pH 7. The solids were then easily removed by decanting, the resulting liquid was completely clear. The turbidity of the supernatant was measured to be less than 5 NTU.

Example 15

This Example illustrates the use of chitosan for the removal of cell mass from a cell culture fluid containing a monoclonal antibody without first adjusting the pH of the starting feedstock.

The starting feed for the experiment is this example was a raw cell culture fluid from an IgG expressing line of Chinese Hamster Ovary (CHO) cells incubated in a Wave bioreactor, the appearance of this liquid was turbid (due to suspended cell mass) and slightly yellow. The pH of the feedstock was about 7.2

Chitosan solution of example 7 was added directly to the starting feedstock, without adjusting the pH of the feedstock, in an amount equivalent to about 0.06% by weight of dry chitosan relative to the volume of the starting feed, the appearance of this sample did not change. The pH of the liquid was then raised to 7.3 by addition of 1N NaOH while mixing. A precipitate was formed, which was easily removed by decanting, the resulting liquid was completely clear. The turbidity of the supernatant was measured to be less than 1 NTU.

Example 16

This Example illustrates the synthesis of poly(4-vinyl pyridine-co-vinyl pyridinium Sulphopropyl betaine), a water soluble polymer for impurity removal.

The polymer was synthesized by the direct reaction of poly(4-vinyl pyridine), PVP, and 1,3 propane sultone, PS, according to a modified literature technique. The polymer was initially dried in a vacuum oven at T=100° C. for 48 hr to remove residual monomer. 3 g of PVP were transferred to the reaction flask and dissolved in 50 ml propylene carbonate (99%) maintained at T=80° C. under a nitrogen atmosphere. 0.18 g of PS was dissolved in 2 ml of propylene carbonate and the solution was then added drop wise to the reaction flask. After the complete addition of the PS solution, the reaction was maintained at 110° C. for 12 hr. The mole ratio of the reactants was selected such that the product comprises 5 mol % of 4-vinyl pyridinium Sulphopropyl betaine. The resulting reaction mixture was cooled down to room temperature and precipitated in excess ethylacetate. The precipitate was dried in a vacuum oven a T=70° C. for 24 hr.

The polymer was characterized using FTIR which revealed the presence of the sulfonate stretches at 1035 $cm^{-1}$ and 1200 $cm^{-1}$.

Example 17

This Example illustrates the removal of negatively charged impurities from a cell culture medium containing a monoclonal antibody using poly(4-vinyl pyridine-co-vinyl pyridinium sulphopropyl betaine).

0.07 g of the copolymer (10 wt %) from example 16 were mixed with 10 ml feedstock after adjusting the pH of the latter to 3.5-4.0 using 0.4 g of 1M HCl. Following 30 min incubation time, the polymer-cell complexes were precipitated by increasing the pH gradually to 5.2 using NaOH (1.0 M). The precipitate was removed by filtration and the pH of the supernatant was adjusted to 7.0.

Following this procedure, 85 wt % of IgG was recovered in the clarified supernatant. The quoted numbers are relative to the initial amount of IgG present in the starting unclarified feedstock.

Example 18

This Example illustrates the synthesis of poly(4-vinyl pyridine-co-vinyl pyridinium ethylene glycol), a water soluble polymer for impurity removal.

The polymer was synthesized by the direct reaction of poly(4-vinyl pyridine), P4VP, and polyethylene glycol diglycidyl ether (Mn 540 g $mol^{-1}$). The polymer was initially dried in a vacuum oven at T=100° C. for 48 hr to remove residual monomer. 10 g of P4VP were transferred to the reaction flask and dissolved in 100 ml methanol, followed by the drop wise addition of 0.1 g of lithium hydroxide dissolved in 10 ml deionized water. A precipitate was observed upon the addition of the lithium hydroxide solution but re-dissolved within minutes of continuous stirring. After adding 0.15 g of polyethylene glycol diglycidyl ether to the reaction flask, the mixture was maintained at 80° C. for 24 hrs. The resulting reaction mixture was then cooled down to room temperature and precipitated in water. The product was further purified by precipitation from an acidic solution by adjusting the solution pH to neutral conditions. The purified polymer was stored in the solution state as 10 wt % in 1M HCl.

Example 19

This Example illustrates the removal of negatively charged impurities from a cell culture medium containing a monoclonal antibody using poly(4-vinyl pyridine-co-vinyl pyridinium ethylene glycol).

0.04 g of the copolymer (10 wt %) from example 18 were mixed with 8 ml feedstock after adjusting the pH of the latter to 3.5 using 0.4 g of 1M HCl. Following 10 min incubation time, the polymer-cell complexes were precipitated by increasing the pH gradually to 5.2 using NaOH (1M). The precipitate was removed by filtration and the pH of the supernatant was adjusted to 7.0. The turbidity of the supernatant was around 90 NTU, while the turbidity of the starting feedstock was 300 NTU.

What is claimed:

1. A method for purifying a monoclonal antibody from a mixture containing a member selected from the group consisting of host cell protein, cell, cell fragment, nucleic acid, virus, pyrogen and endotoxin impurities comprising:
   a. providing the mixture at a set pH,
   b. adding to said mixture one or more polymers selected from the group consisting of polyvinylpyridine and copolymers of vinyl pyridine solubilizable in said mixture under the set pH,
   c. mixing the one or more solubilized polymers throughout the mixture;
   d. precipitating the one or more polymers and one or more bound impurities out of solution by changing the pH in the mixture; and
   e. recovering the monoclonal antibody.

2. The method of claim 1 wherein the one or more polymers are solubilized in carrier liquid before said addition the mixture.

3. The method of claim 1 wherein the one or more polymers is caused to be soluble in said mixture due to a pH level below 7.

4. The method of claim 1 further comprising the step of incorporating the recovered monoclonal antibody into a pharmaceutical formulation.

5. The method of claim 1 wherein, prior to step b., the one or more polymers are added to a carrier liquid under conditions that cause the one or more polymers to go into solution, and the carrier liquid containing the one or more polymers in solution is added to the mixture in step b. through a static mixer.

6. The method of claim 1 further comprising the step in which the recovered monoclonal antibody is formulated in a pharmaceutically acceptable carrier for a purpose selected from the group consisting of research, diagnostic and therapeutic purposes.

7. The method of claim 1 wherein the one or more polymers are added in excess to the mixture, relative to the amount of impurities in said mixture, and recovered as a precipitate.

8. The method of claim 1 further comprising:
   subjecting the recovered monoclonal antibody to a second purification step in which a pH stimuli responsive soluble polymer which is capable of binding to the monoclonal antibody is added to a mixture containing the recovered monoclonal antibody from the method of claim 1 under conditions to cause the polymer to be in solution,
   the pH conditions are changed so as to cause the polymer to precipitate out of solution with the recovered monoclonal antibody,
   recovering the precipitate,
   eluting the monoclonal antibody from the precipitate and recovering the monoclonal antibody.

9. The method of claim 1 further comprising:
   subjecting the recovered monoclonal antibody to a second purification step in which a stimuli responsive soluble polymer which is capable of binding to the monoclonal antibody is added to a mixture containing the recovered monoclonal antibody from the method of claim 1 under conditions to cause the polymer to be in solution, the conditions are changed so as to cause the polymer to precipitate out of solution with the recovered monoclonal antibody, recovering the precipitate, washing the precipitate at least one time, eluting the monoclonal antibody from the precipitate and recovering the monoclonal antibody.

10. The method of claim 1 wherein the monoclonal antibody is recovered by separating the one or more precipitated polymers and impurities from the mixture.

11. The method of claim 1 wherein the one or more polymers are capable of binding with one or more of the impurities in the solubilized and precipitated state.

12. The method of claim 1, wherein said monoclonal antibody is a chimeric antibody.

13. The method of claim 1, wherein said monoclonal antibody is a humanized antibody.

14. The method of claim 1, wherein said polymer is selected from the group consisting of poly(4-vinyl pyridine-co-vinyl pyridinium sulphopropyl betaine) and poly(4-vinyl pyridine-co-vinylpyridinium ethylene glycol).

15. The method of claim 14, wherein the step of changing the pH in step d comprises raising the pH to 5.2.

16. A method for purifying a monoclonal antibody from a mixture containing a host cell protein as an impurity comprising:
   a. providing an initial mixture of a monoclonal antibody from a mixture containing a host cell protein as an impurity, said initial mixture having an initial purity,
   b. conducting a purification step by adding to said mixture a carrier liquid containing one or more polymers selected from the group consisting of polyvinylpyridine and copolymers of vinyl pyridine solubilized in said carrier liquid, the polymer being soluble at a pH within the carrier liquid and the mixture and being capable of binding to the impurity;
   c. allowing the one or more polymers to mix with the constituents of the mixture;
   d. precipitating the one or more polymers and host cell protein of the mixture out of solution by changing said pH in the mixture thereby causing the one or more polymers to be insoluble;
   e. filtering the precipitated one or more polymers from the mixture; and
   f. recovering the monoclonal antibody at a purity at least 1 LRV better than said initial purity.

* * * * *